(12) United States Patent
Kim et al.

(10) Patent No.: US 8,058,312 B2
(45) Date of Patent: Nov. 15, 2011

(54) N, N-DIMETHYL IMIDODICARBONIMIDIC DIAMIDE ACETATE, METHOD FOR PRODUCING THE SAME AND PHARMACEUTICAL COMPOSITIONS COMPRISING THE SAME

(75) Inventors: Sung Wuk Kim, Seongnam-si (KR); Sung Soo Jun, Seongnam-si (KR); Young Gwan Jo, Eullim (KR); Ja Seong Koo, Daejeon (KR); Young Woong Kim, Daejeon (KR)

(73) Assignee: Hanall Biopharma Co., Ltd., Daejeon (KR)

( * ) Notice: Subject to any disclaimer, the term of this patent is extended or adjusted under 35 U.S.C. 154(b) by 0 days.

(21) Appl. No.: 12/524,695

(22) PCT Filed: Jan. 29, 2008

(86) PCT No.: PCT/KR2008/000529
§ 371 (c)(1),
(2), (4) Date: Nov. 10, 2009

(87) PCT Pub. No.: WO2008/093984
PCT Pub. Date: Aug. 7, 2008

(65) Prior Publication Data
US 2010/0087544 A1 Apr. 8, 2010

(30) Foreign Application Priority Data

Jan. 29, 2007 (KR) .................. 10-2007-0008835

(51) Int. Cl.
*A01N 37/52* (2006.01)
*A61K 31/155* (2006.01)
*C07C 277/00* (2006.01)
*C07C 279/00* (2006.01)

(52) U.S. Cl. ........................ 514/635; 564/233
(58) Field of Classification Search .............. 514/635; 564/233
See application file for complete search history.

(56) References Cited

U.S. PATENT DOCUMENTS

| | | | |
|---|---|---|---|
| 3,174,901 A | 3/1965 | Sterne | |
| 3,957,853 A | 5/1976 | Bohuon | |
| 4,028,402 A | 6/1977 | Fischer et al. | |
| 4,080,472 A | 3/1978 | Bohuon | |
| 4,835,184 A | 5/1989 | Hugelin et al. | |
| 4,879,303 A | 11/1989 | Davison et al. | |
| 6,031,004 A | 2/2000 | Timmins et al. | |
| 6,340,475 B2 | 1/2002 | Shell et al. | |
| 6,475,521 B1 | 11/2002 | Timmins et al. | |
| 6,635,280 B2 | 10/2003 | Shell et al. | |
| 6,660,300 B1 | 12/2003 | Timmins et al. | |
| 2001/0018070 A1 | 8/2001 | Shell et al. | |
| 2002/0051820 A1 | 5/2002 | Shell et al. | |
| 2003/0039688 A1 | 2/2003 | Shell et al. | |
| 2005/0256195 A1 | 11/2005 | Tayama et al. | |

FOREIGN PATENT DOCUMENTS

| | | |
|---|---|---|
| EP | 0283369 A2 | 9/1988 |
| FR | 2220256 A1 | 10/1974 |
| KR | 100090479 | 11/1987 |
| KR | 1999-7011439 | 12/1999 |
| KR | 2000-7010280 | 9/2000 |
| KR | 2004-7013025 | 8/2004 |
| WO | 98-55107 A1 | 12/1998 |
| WO | 99-47128 A1 | 9/1999 |
| WO | 0191696 | 6/2001 |
| WO | 0211721 A1 | 2/2002 |
| WO | WO 03/028704 | 4/2003 |
| WO | 03074039 A1 | 9/2003 |
| WO | 2005/018626 A1 | 3/2005 |
| WO | 2005092311 A1 | 10/2005 |

OTHER PUBLICATIONS

PCT Written Opinion of the International Searching Authority of international application No. PCT/KR2008/000529, dated May 16, 2008 (5 pages).
PCT International Preliminary Report on Patentability of international application No. PCT/KR2008/000529, dated Apr. 20, 2009 (4 pages).
International Search Report for PCT/KR2008/000529 dated May 16, 2008.
Buzzai, et al; "Systemic Treatment with the Antidiabetic Drug Metformin Selectively Impairs p53-Deficient Tumor Cell Growth," Cancer Res 2007; 67: (14), Jul. 15, 2007, pp. 6745-6752.
Hanai, et al; "The muscle-specific ubiquitin ligase atrogin-1/MAFbx mediates statin-induced muscle toxicity," The Journal of Clinical Investigation, vol. 117, No. 12, Dec. 2007, pp. 3940-3951.
Marathe, et al; "Effect of altered gastric emptying and gastrointestinal motility on metformin absorption," British Journal of Clinical Pharmacology, vol. 50, 2000, pp. 325-332.
Carol S. Johnston and Cindy A. Gaas; "Vinegar: Medicinal Uses and Antiglycemic Effect," Medscape General Medicine, 2006, pp. 1-12.
Ogawa, et al; "Acetic Acid Suppresses the Increase in Disaccharidase Activity That Occurs during Culture of Caco-2 Cells," The Journal of Nutrition, Mar. 2000, vol. 130, pp. 507-513.
Ostman, et al.; "Vinegar supplementation lowers glucose and insulin responses and increases satiety after a bread meal in healthy subjects," European Journal of Clinical Nutrition, Sep. 2005, vol. 59, No. 9, pp. 983-988.

(Continued)

*Primary Examiner* — Sreeni Padmanabhan
*Assistant Examiner* — Samira Jean-Louis
(74) *Attorney, Agent, or Firm* — Heslin Rothenberg Farley & Mesiti P.C.

(57) ABSTRACT

The present invention relates to N,N-dimethyl imidodicarbonimidic diamide acetate, a method of preparing the same and a pharmaceutical composition comprising the same, and more particularly, to N,N-dimethyl imidodicarbonimidic diamide acetate which is a crystalline acid addition salt prepared by reacting N,N-dimethyl imidodicarbonimidic diamide with acetic acid, and which is very effective as a therapeutic agent for treating metabolic syndromes that glycosuria and diabetes mellitus, obesity, hyperlipidemia, fatty liver, coronary heart disease, osteoporosis, polycystic ovarian syndrome, a cancer depleted of gene P53, etc. are complexly occurred; treating diabetes mellitus and preventing its complication; and treating a cancer and preventing myalgia, muscle cell cytotoxicity and rhabdomyolysis, etc. since the acid addition salt is excellent in physicochemical properties such as solubility, stability, non-hygroscopicity, anti-adhering property, etc., and low toxicity, a method of preparing the same and a pharmaceutical composition comprising the same.

17 Claims, 10 Drawing Sheets

OTHER PUBLICATIONS

Johnston, et al.; "Vinegar Improves Insulin Sensitivity to a High-Carbohydrate Meal in Subjects With Insulin Resistance or Type 2 Diabetes," Diabetes Care, vol. 27, No. 1, Jan. 2004, pp. 281-282.

Leeman, et al.; "Vinegar dressing and cold storage of potatoes lowers postprandial glycaemic and insulinaemic responses in healthy subjects," European Journal of Clinical Nutrition, Nov. 2005, vol. 59, No. 11, pp. 1266-1271.

Kiyoshi Ebihara and Akira Nakajima; "Effect of Acetic Acid and Vinegar on Blood Glucose and Insulin Responses to Orally Administered Sucrose and Starch," Agricultural and Biological Chemistry, 1988, vol. 52, No. 5, pp. 1311-1312.

Brighenti, et al.; "Effect of neutralized and native vinegar on blood glucose and acetate responses to a mixed meal in healthy subjects," European Journal of Clinical Nutrition, Apr. 1995, vol. 49, No. 4, pp. 242-247.

(1013) M-001

N, N-DIMETHYL IMIDODICARBONIMIDIC DIAMIDE ACETATE, METHOD FOR PRODUCING THE SAME AND PHARMACEUTICAL COMPOSITIONS COMPRISING THE SAME

CROSS REFERENCE TO RELATED APPLICATION

This application is the National Phase filing of International Application No. PCT/KR2008/000529, filed Jan. 29, 2008, which claims priority to Korean Application No. 10-2007-0008835, filed Jan. 29, 2007. The entire content of each prior application is hereby incorporated by reference.

TECHNICAL FIELD

The present invention relates to N,N-dimethyl imidodicarbonimidic diamide acetate, a method of preparing the same and a pharmaceutical composition comprising the same, and more particularly, to N,N-dimethyl imidodicarbonimidic diamide acetate which is a crystalline acid addition salt prepared by reacting N,N-dimethyl imidodicarbonimidic diamide with acetic acid, and which is very effective as a therapeutic agent for treating metabolic syndromes that glycosuria and diabetes mellitus, obesity, hyperlipidemia, fatty liver, coronary heart disease, osteoporosis, polycystic ovarian syndrome, a cancer depleted of gene P53, etc. are complexly occurred; treating diabetes mellitus and preventing its complication; and treating a cancer and preventing myalgia, muscle cell cytotoxicity and rhabdomyolysis, etc. since the acid addition salt is excellent in physicochemical properties such as solubility, stability, non-hygroscopicity, anti-adhering property, etc., and low toxicity, a method of preparing the same and a pharmaceutical composition comprising the same.

More particularly, the present invention relates to novel N,N-dimethyl imidodicarbonimidic diamide acetate that lowers dissolution rate and improves the permeability to enhance its bioavailability in a lower gastrointestinal tract.

BACKGROUND ART

N,N-dimethyl imidodicarbonimidic diamide has general name of metformin, and is a therapeutic agent for Non-Insulin Dependent Diabetes Mellitus, and a biguanide based pharmaceutical that is most excellent in hypoglycemic action and preventing the complication.

It was suggested in various articles that only metformin has a property as the first choice as oral anti-diabetic agent. In particular, the clinical effect of the metformin was proved by its pharmacological action as AMPK activator. It was reported that AMPK is a key enzyme controlling the metabolism of carbohydrate and lipid physiologically; metformin activates this enzyme, thereby normalizing high blood-glucose level, improving lipid state, normalizing menstrual irregularity, in ovulation, and treating a fatty liver; and metformin is effective in treating or preventing a cancer depleted of gene P53.

Abramson Cancer Center of Medical college, Pennsylvania reported through a professional journal for cancer that metformin is effective as AMPK activator in treating or preventing a cancer depleted of gene P53 [Monica Buzzai, et al. Systemic Treatment with the Antidiabetic Drug Metformin Selectively Impairs p53-Deficient Tumor Cell Growth, Cancer Res 2007; 67:(14). Jul. 15, 2007].

In other words, if a human body is subjected to an unfavorable condition, metformin activates AMPK enzyme, which controls an energy metabolism applied to the condition, thereby controlling glucose and lipid, and removing cancer cells.

Gene P53 renders a damaged cell or an unnecessary cell and an aged cell to kill itself (apoptosis). If a cancer cell is mutated, the gene P53 is depleted, thereby forming incurable cancer cell.

It was verified from experiments that metformin activates the AMPK enzyme of an incurable cancer cell depleted of the gene P53, thereby changing the metabolic path, and accordingly, the cancer cell is killed since it could not adapt itself to the changed metabolic path.

The report suggests that gene P53 removes a cancer and maintains longevity by employing an energy metabolism control enzyme named as AMPK.

Metformin is a drug that activates the AMPK thereby normalizing glucose and lipid metabolism. It was found that if metformin is administered to a cancer depleted of the gene P53, the energy metabolic path for the cancer cell is changed, and anticancer action increases proportionally to a dosage of metformin, and further metformin is effective in treating a cancer in a normal dosage for treating diabetes mellitus.

Further, researchers of the medical center of Beth Israel Deaconess, Boston, United States reported through a professional medical journal that metformin is effective as PGC-1α activator in preventing severe side effects such as myalgia, muscle cell damage and rhabdomyolysis [Jun-ichi Hanai, et al. The muscle-specific ubiquitin ligase atrogin-1/MAFbx mediates statin-induced muscle toxicity, J. Clin. Invest. 117: 3940-3951 (2007)].

Expression of Atrogin-1 gene causes muscle toxicity such as myalgia, muscle cell damage and rhabdomyolysis, but metformin inhibits the expression of Atrogin-1 gene due to PGC-1α transcription factor activity, thereby inhibiting and preventing muscle disorder due to the increase of the expression of Atrogin-1 gene.

Metformin is administered in the form of pharmaceutically acceptable acid addition salt since metformin is pharmaceutically useful in the form of a free base, but the stability of the form is low.

Korean Patent No. 90,479 describes that four physicochemical standards such as (1) excellent solubility; (2) excellent stability; (3) non-hygroscopicity; and (4) the processability as a tablet form must be satisfied for preparing in the form of pharmaceutically acceptable salt. It is very difficult to satisfy the four standards as a pharmaceutically acceptable acid addition salt.

Research for addition salt other than metformin hydrochloride has been performed. U.S. Pat. No. 3,957,853 discloses metformin acetyl salicylic acid salt, U.S. Pat. No. 4,028,402 discloses a novel addition salt of biguanide compound, and U.S. Pat. No. 4,080,472 discloses the preparation of metformin chlorfibric acid salt and treatment of diabetes mellitus related diseases. Further, U.S. Pat. No. 6,031,004 describes a medical composition by fumarate, succinate and maleinic acid of metformin, and its use. Although the research for metformin addition salt has been continuously performed, metformin is approved in only a drug as hydrochloride, and is widely prescribed as a therapeutic agent for non-insulin dependent diabetes mellitus. Metformin hydrochloride is the material that is almost exclusively absorbed in upper small intestine. Accordingly, it is incompletely absorbed in lower small intestine, and thus it is a salt very difficult to formulate as a controlled release drug for 24 hours. This is why the solubility of metformin hydrochloride is high (Marathe, P. et al., Br. J. Clin. Pharmacol., 50:325-332 (2000)).

Research for addition salt other than metformin hydrochloride has been performed. U.S. Pat. No. 3,957,853 discloses metformin acetyl salicylic acid salt, U.S. Pat. No. 4,028,402 discloses a novel addition salt of biguanide compound, and U.S. Pat. No. 4,080,472 discloses the preparation of metformin chlorfibric acid salt and treatment of diabetes mellitus related diseases. Further, U.S. Pat. No. 6,031,004 describes a medical composition by fumarate, succinate and maleinic acid of metformin, and its use. However, the preparation method and composition of metformin acetate had not been mentioned in the prior patents. Further, there is no known or progressed research for the effect of metformin acetate.

Although the research for metformin addition salt has been continuously performed, only metformin hydrochloride is actually used. Hydrochloride salt is large in its unit dosage and its formulation size is very large. Accordingly, even though a novel addition salt is attempted, its molecular weight and formulation becomes too large, and thus it is inferred that it is difficult to formulate. Accordingly, it is considered that the development of a product for a novel addition salt had not been attempted.

Meanwhile, prior patent (U.S. Pat. No. 4,080,472) describes that when metformin free base is prepared, an ion exchange resin column is used for removing hydrochloric acid from metformin hydrochloride, and prior patent describes that severe preparation condition that a solvent is refluxed with heating and filtered in hot state is required.

The usual dosage of metformin hydrochloride is 2550 mg at maximum daily, i.e., 500 mg or 750 mg tablet is administered 2~3 times with a diet a day.

Such an administration method causes drastic changes in the drug level in blood due to the properties of metformin hydrochloride having quick drug elimination rate, and such a change in drug level in blood can result in side effects and resistance to the drug. Actually, the side effects related to the use of metformin hydrochloride occur frequently in gastrointestinal tract, and the examples include anorexia, nausea, vomiting and occasionally diarrhea. Accordingly, a research for extended controlled release formulation of metformin hydrochloride is being progressed in order to decrease such side effects and improve the treating quality of the Type 2 diabetic patients.

Further, metformin hydrochloride is highly water soluble drug (>300 mg/mL, 25☐), and thus if it is not designed as special formulation, excessive drop in blood glucose by drastic release phenomecan be caused. Accordingly, it is considered that a controlled release tablet designed so that defined dose of the drug can be control-released for 24 hours is preferable administration form in the aspect of a patient's convenience as well as therapeutic effect.

However, metformin hydrochloride is highly soluble in water, and hardly permeates the lower gastrointestinal tract, and thus the most drug must be absorbed at upper gastrointestinal tract. Therefore, there are many problems in preparation technology for preparing special formulation for controlled release.

Many patents for controlled release tablet of metformin for overcoming such problems in the pharmaceutical technology are registered at home and abroad. Korean Patent Application No. 1999-7011439 filed in the name of Depomed Inc. describes a controlled release formulation that releases a drug for 8 hours using general high molecular polymer as a formulation for controlled release of a soluble drug. Korean Patent Application No. 2000-7010280 filed in the name of Bristol Meyer's Squibb describes 2 phase controlled release tablet suitable for controlled release of metformin having high solubility in a desired degree.

However, since the unit dosage of metformin is large, i.e., 500 to 750 mg, the total weight of the tablet is very heavy in consideration of adding a pharmaceutical excipient including a controlled release agent. Further, since the solubility of metformin hydrochloride is high, the controlled release agent to be added is also needed in much amount in order to controlled-release for desired time, and accordingly the formulation may be too large to take easily. Accordingly, it is not easy to maintain continuous controlled release of metformin hydrochloride within the size that a patient can take the tablet.

The reason why metformin acetate is selected as an antidiabetic agent is that it can cause pharmaceutically excellent controlled release and the pharmacological effect of metformin acetate is superior to that of metformin hydrochloride.

Recently, researches for various pharmacological effects of acetate are actively progressed. Many experiments that small amount of vinegar lowers blood glucose at 30 minutes after meal by inhibiting an enzyme to degrade disaccharide to glucose in intestine have been reported.

Recently, research by Carol Johnston et al for the effect of vinegar performed for patients having type 2 diabetes mellitus mentioned that 64% of blood glucose after meal is decreased and 34% of insulin sensitivity is also decreased in vinegar administration group among insulin resistant group [Vinegar: Medicinal uses and Antiglycemic effect Carol Johnston, et al. Medscape general medicine 2006; 8(2):61].

Further, Ogawa mentioned that acetic acid inhibits the activity of disaccharidase such as sucrase and lactase. In other words, he mentioned that acetic acid plays a role in decreasing blood glucose by inhibiting the action of an enzyme degrading polysaccharide to monosaccharide.

REFERENCES

1. Ogawa N, Satsu H, Watanabe H, et al. Acetic acid suppresses the increase in disaccharidase activity that occurs during culture of caco-2 cells. J. Nutr. 2000 March; 130(3): 507-13
2. Carol S. Johnston, PhD, R D; Cindy A. Gaas, BS. Vinegar: Medicinal Uses and Antiglycemic Effect, Medscape General Medicine. 2006; 8(2):61.
3. Ostman E, Granfeldt Y, Persson L, Björck I. Vinegar supplementation lowers glucose and insulin responses and increases satiety after a bread meal in healthy subjects. Eur J Clin Nutr. 2005 September; 59(9), 983-8.
4. Johnston C S, Kim C M, Buller A J. Vinegar improves insulin sensitivity to a high carbohydrate meal in subjects with insulin resistance or type 2 diabetes. Diabetes Care. 2004 January; 27(1):281-2.
5. Leeman M, Ostman E, Björck I. Vinegar dressing and cold storage of potatoes lowers postprandial glycaemic and insulinaemic responses in healthy subjects. Eur J Clin Nutr. 2005 November; 59(11):1266-71.
6. Ebihara K, Nakajima A. Effect of acetic acid and vinegar on blood glucose and insulin responses to orally administered sucrose and starch.
Agric Biol. Chem. 1988; 52:1311-1312.
7. Brighenti F, Castellani G, Benini L, et al. Effect of neutralized and native vinegar on blood glucose and acetate responses to a mixed meal in healthy subjects. Eur J Clin Nutr. 1995 April; 49(4):242-7.

Korean Patent Application No. 2004-7013025 filed by Mitsukan Company, Japan describes a food and medical composition for preventing hypertension characterized in that minute amount of acetic acid shows excellent action of lowering blood pressure by oral intake for a long period.

Researches for vinegar and acetic acid itself on various diseases have been actively performed. However, the research shows considerable effects as outcome of the research for vinegar as food not experiment for acetate, it did not show the effect as metformin acetate as shown in the present invention, and it did not mentioned the effect for interaction with metformin.

The present inventors decided that departing from the paradigm that the problem of metformin hydrochloride must be overcome by designing a formulation through selecting a proper controlled release agent, if the solubility of the active ingredient is lowered, side effects such as excessive drop of blood glucose level or a disorder in gastrointestinal tract is improved even on taking immediately release tablet, and more efficient controlled release can be performed on formulating the immediately release preparation; and studied on metformin addition salt having relatively low solubility to water. However, there is a problem in practicability since if the molecular weight of a novel metformin derivative is very high compared to metformin hydrochloride even though a metformin derivative having low solubility is synthesized, the dosage of metformin is increased. This is a crucial problem on considering the unit dosage of metformin is large. If a metformin addition salt, which has not too large molecular weight thereby having dosage capable of being compressed as a tablet, is easy to be control-released due to lowered solubility, and has relatively excellent permeability at lower gastrointestinal tract and colon, and thus has relatively wide absorption site compared to metformin hydrochloride, is developed, it will have excellent ripple effect pharmaceutically or pharmaco-dynamically.

DISCLOSURE OF INVENTION

Technical Problem

The present inventors decided that departing from the paradigm that the problem of metformin hydrochloride must be overcome by designing a formulation through selecting a proper controlled release agent, if the solubility of the active ingredient is lowered, side effects such as excessive drop of blood glucose level or a disorder in gastrointestinal tract is improved even on taking immediately release tablet, and the control of drug release can be performed more efficiently; and studied on metformin addition salt having relatively low solubility to water. However, if the molecular weight of a novel metformin derivatives is very high compared to metformin hydrochloride, there is a problem in practicability even though a metformin derivative having low solubility is synthesized, because of the increased dosage of metformin. This is a crucial problem on considering the unit dosage of metformin is large. If a metformin addition salt, which has not too large molecular weight thereby having dosage capable of being compressed as a tablet, is easy to control the drug release rate due to lowered solubility, and has relatively excellent permeability at lower gastrointestinal tract and colon, and thus has relatively wide absorption site compared to metformin hydrochloride, is developed, it will have excellent ripple effect pharmaceutically or pharmaco-dynamically.

If the pharmacological effect of the addition salt can show the synergic effect with the active pharmacological ingredient of metformin, it will be more idealistic metformin addition salt. From the result of a continuous research, the present inventors completed the present invention by discovering metformin acetate having not too large molecular weight and having relatively low solubility.

Further, the present inventors performed various clinical researches for metformin acetate, and discovered that the metformin acetate has pharmaceutical and pharamacokinetic advantage attainable due to low solubility, and is relatively more excellent compared to metformin hydrochloride in the effects of initial drop in blood glucose and drop in blood glucose after meal. This suggests that even though the unit dosage of metformin acetate less than that of metformin hydrochloride is administered, the same clinical effect as metformin hydrochloride can be obtained, and accordingly its excellent ripple effect can be also expected pharmacologically.

Therefore, the object of the present invention is to provide pharmaceutically acceptable metformin acetate having excellent physicochemical properties such as solubility and stability, and a method of preparing the same.

Further, another object of the present invention is to provide a pharmaceutical composition for treating or preventing diabetes mellitus and its complication comprising metformin acetate as an active ingredient.

Still another object of the present invention is to provide a pharmaceutical composition for treating or preventing diabetes mellitus and its complication comprising metformin acetate having relatively low solubility in water as an active ingredient.

Still another object of the present invention is to provide a method of preparing metformin acetate.

Still another object of the present invention is to provide an immediately release or controlled release metformin formulation comprising metformin acetate as an active ingredient, which controls excellent drug release even using less controlled release agent compared to metformin hydrochloride, and has more clinically excellent effects of initial drop in blood glucose and drop in blood glucose after meal than that of metformin hydrochloride.

Further, the absorption speed of metformin in gastrointestinal tract can be controlled by extending the gastric retention time of a drug through using metformin as an active ingredient and a matrix agent capable of controlling the release rate of the metformin. Therefore, the size of a tablet can be designed in a small level suitable to take since the release of the drug is continuously and sufficiently achieved for 24 hours even when the controlled release matrices according to the present invention are formulated in less amounts than that of the matrices required in preparing previous controlled release tablet.

Technical Solution

The present inventors completed the present invention by preparing metformin acetate, a method of preparing the same and a composition comprising the same useful as a therapeutic agent for diabetes mellitus The present invention is comprised of the following twelve characteristic features:

(1) metformin acetate represented by formula 1 below;

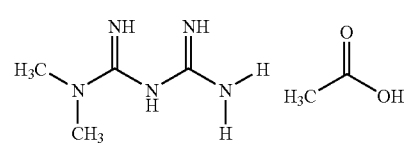

[Formula 1]

(2) metformin acetate according to the above (1) in the form of anhydrous, hemihydrate or monohydrate;

(3) a method of preparing the metformin acetate of formula 1 comprising reacting 1 equivalent of the metformin hydrochloride of formula 4 below with 1 to 2 equivalent of inorganic base in water or an organic solvent to generate metformin free base; and then reacting with 1 to 2 equivalent of acetic acid of formula 2 below with or without removing the inorganic salt;

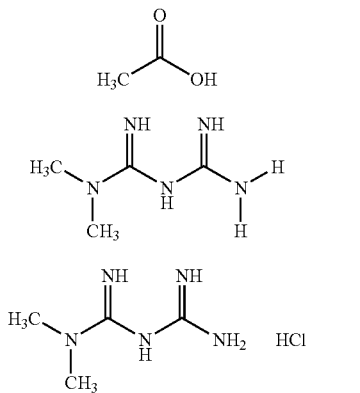

[Formula 2]

[Formula 3]

[Formula 4]

(4) a method of preparing the metformin acetate of formula 1 comprising reacting 1 equivalent of the metformin hydrochloride of formula 4 with 1 to 2 equivalents of an organic alkali in water, and then reacting with acetic acid of formula 2 without removing inorganic salt;

(5) a method of preparing the metformin acetate of formula 1 comprising reacting 1 equivalent of the metformin hydrochloride of formula 4 with 1 to 2 equivalents of inorganic base or an organic alkali in water, and then reacting with 1 to 2 equivalents of acetic acid of formula 2 without removing inorganic salt;

(6) the method of preparing the metformin acetate according to the above (3) or (4) comprising reacting 1 equivalent of metformin free base with 1 equivalent of acetic acid;

(7) the method of preparing the metformin acetate according to the above (3) wherein the organic solvent is selected from the group consisting of methanol, ethanol, isopropanol, acetone and acetonitrile;

(8) the method of preparing the metformin acetate according to the above (3) wherein 1 equivalent of metformin hydrochloride and 1 to 2 equivalents of inorganic base are reacted in water or an organic solvent to generated metformin free base;

(9) a pharmaceutical composition comprising the metformin acetate of the above (1) as an active ingredient, for treating diabetes mellitus of patients having metabolic syndromes that glycosuria and diabetes mellitus, obesity, hyperlipidemia and coronary heart disease are complexly occurred, and preventing its complication;

(10) the pharmaceutical composition according to the above (9) wherein the composition is formulated in the form of a tablet or a capsule;

(11) the pharmaceutical composition according to the above (10) wherein the composition further comprises a pharmaceutically acceptable carrier, a diluent or an excipient; and

(12) the pharmaceutical composition according to the above (9), (10) or (11) wherein the composition is effective in preventing and treating type 2 diabetes mellitus, controlling body weight, lowering hyperlipidemia lipid, treating fatty liver, preventing coronary heart disease, treating polycystic ovarian syndrome, treating a cancer depleted of gene P53, and preventing myalgia, muscle cell cytotoxicity and rhabdomyolysis by orally administering 50 to 3,000 mg of the metformin acetate of formula 1 as a free base a day over 1 to 3 times.

Advantageous Effects

Metformin acetate according to the present invention gives more excellent drop effect in blood glucose level than that of metformin hydrochloride used previously as an anti-diabetic agent, and in particular, gives very excellent drop effect in blood glucose level before meal as well as after meal, and increases insulin sensitivity. More particularly, the metformin acetate gives pharmaceutically and phamacodynamically excellent effect showing effective control of a drug release by lowering solubility compared to that of the metformin hydrochloride. Further, the metformin acetate according to the present invention is proper in the size of molecular weight, and superior in pharmaceutical, pharmacological or clinical aspects to metformin hydrochloride. The metformin acetate according to the present invention is slowly released in small intestine on oral intake, and is simultaneously separated to metformin and acetic acid, and then metformin is absorbed and acetic acid inhibits the degradation of disaccharide in small intestine thereby inhibiting rise in blood glucose level. The metformin acetate is a compound pharmaceutically very excellent to show optimum bioavailability.

Further, the method of preparing the metformin acetate according to the present invention established the steps so that it can be progressed simply and without special equipment. The method of preparing the metformin acetate according to the present invention can synthesize a novel metformin salt with a low cost by improving the steps simply thereby elevating industrial applicability so that the synthesis can be performed in general production equipment without special equipment.

The metformin acetate according to the present invention is a crystalline acid addition salt suitable for preparing a pharmaceutical formulation compared to previous metformin hydrochloride prepared by using hydrochloric acid, which is a biguanide compound using only one salt as drug. Further, the metformin acetate is a novel drug that increases pharmaceutical and physicochemical advantages such as stability, non-hygroscopicity and processability as a tablet formulation, as well as increases the therapeutic effect for diabetes mellitus and its complication even though acetic acid having relatively low toxicity compared to that of the metformin hydrochloride is used.

Table 1 below compares the oral toxicity of hydrochloric acid forming a crystalline acid addition salt of the metformin hydrochloride and acetic acid forming a crystalline acid addition salt of the metformin acetate. The toxicity data for two acids were excerpted from Registry of Toxic Effects of Chemical Substances (RTECS) Data.

TABLE 1

| Acid | Administration path | Subject animal | Dose (LD50) | Dose (TDLo) |
|---|---|---|---|---|
| Hydrochloric acid | Intraperitoneal | Mouse | 40 mg/kg | — |
| | Oral | Rabbit | 900 mg/kg | — |
| Acetic acid | Intravenous | Mouse | 525 mg/kg | — |
| | Oral | Rat | 3,310 mg/kg | — |
| | Oral | Human being | — | 1,470 µg/kg |

LD50: 50% lethal dose,
TDLo; lowest toxic dose

As indicated in the Table 1, hydrochloric acid used in preparing a crystalline acid addition salt of the metformin is toxic itself, but acetic acid used in the present invention is very safe compared to hydrochloric acid. From in vivo and in vitro experiments for the pharmacological effect of the metformin acetate performed in several ways, it could be anticipated that the metformin acetate is more excellent compared to the metformin hydrochloride in the effect of drop in blood glucose, action of decreasing lipid and improvement in metabolic syndrome, as well as therapeutic purpose can be achieved even with less dosage than the metformin hydrochloride.

MODE FOR INVENTION

Figure 1:
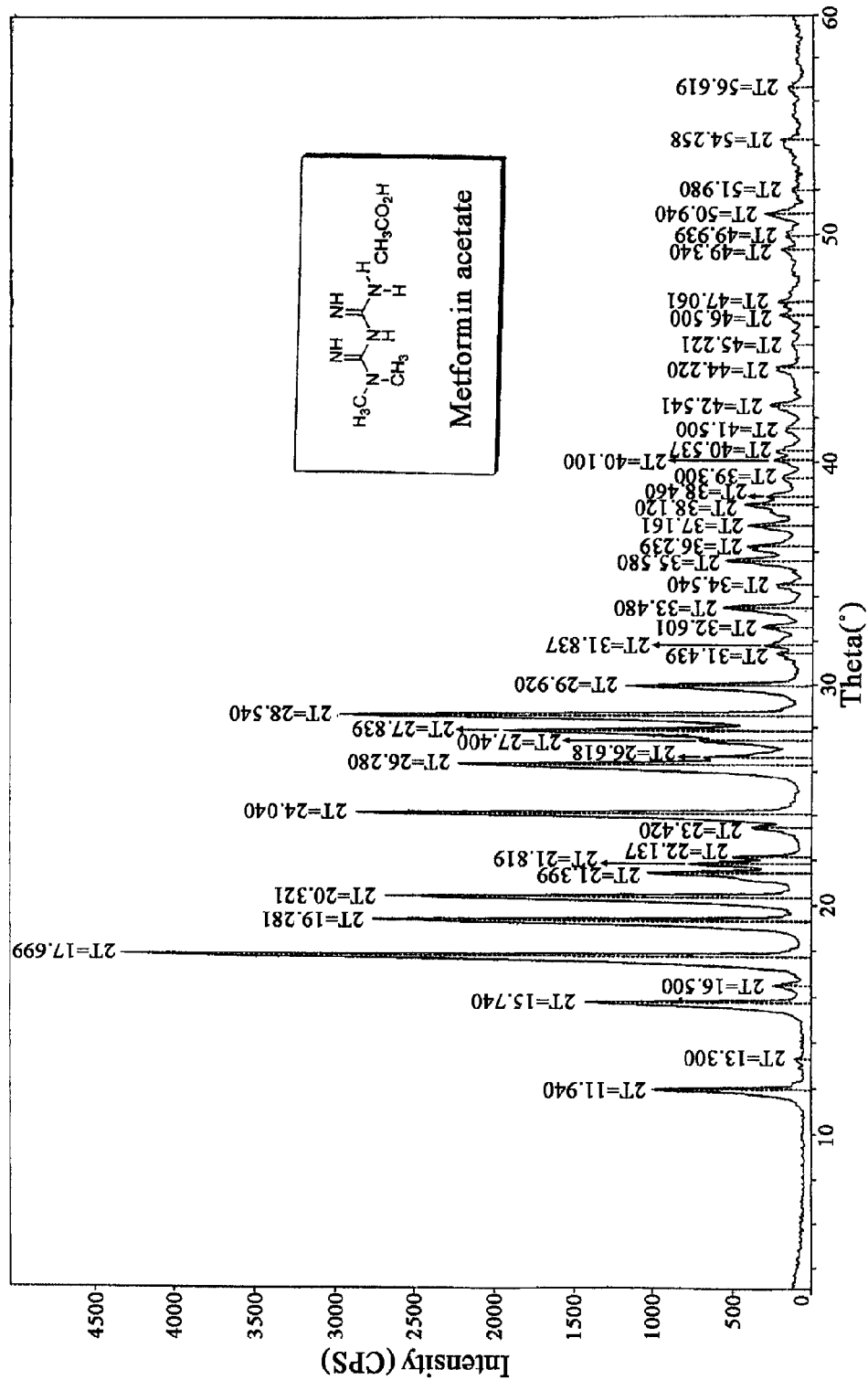
FIG. 1 is the result of XRD measurement for metformin acetate of Example 1 according to the present invention.

The present invention relates to novel metformin acetate of formula 1 below that is more superior in the physicochemical properties such as solubility, stability, non-hygroscopicity and processability as a tablet formulation, and is more effective in treating or preventing diabetes mellitus and its complication:

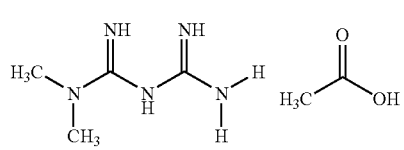

[Formula 1]

Further, the present invention provides a method of preparing metformin acetate of formula 1 comprising adding a base to the metformin hydrochloride of formula 4 in water or an organic solvent to generate metformin free base represented by formula 3 below; and reacting the resulting metformin free base with acetic acid represented by formula 2 below, as described in reaction scheme 1 below:

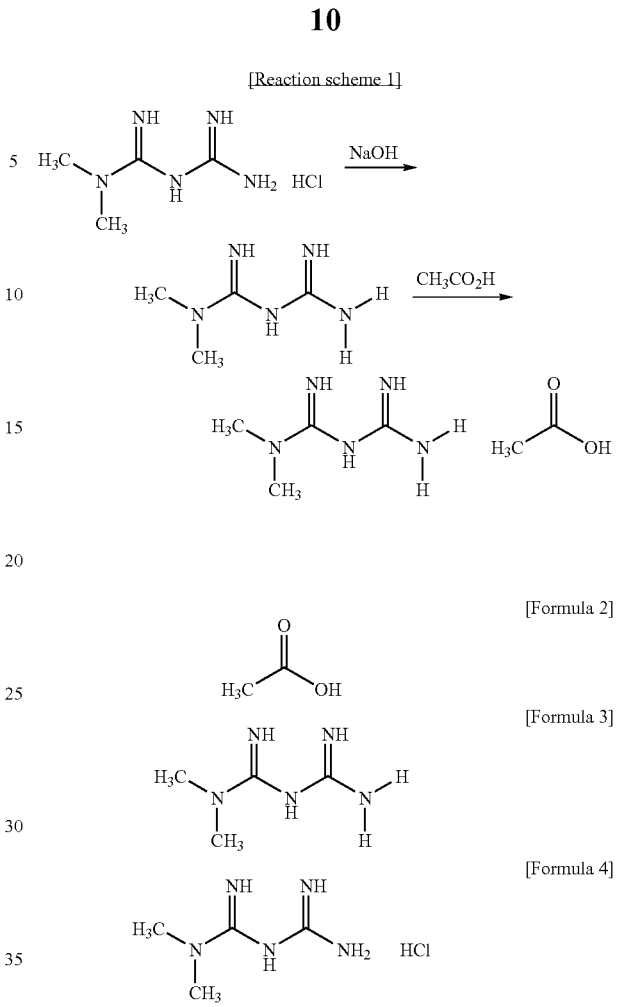

The preparation method as described in the reaction scheme 1 comprises
1) removing the addition salt of the metformin hydrochloride of formula 4;
2) adding acetic acid of formula 2 to a reaction solution of the metformin of formula 3 to prepare a mixture; and
3) stirring the mixture, and filtering, washing and drying the resulting solid to form a novel crystalline acid addition salt of formula 1.

The crystalline acid addition salt of the metformin according to the present invention is prepared by adding acetic acid to a solution containing metformin represented by formula 3 comprising the following steps.

In the first step, inorganic base can be used under water or an organic solvent condition in order to obtain metformin free base. The examples of the inorganic base include alkali hydroxide such as sodium hydroxide and potassium hydroxide, and sodium hydroxide is preferably used. 1 to 2 equivalents of the inorganic base can be used for 1 equivalent of metformin hydrochloride.

In the second step adding acetic acid to a reaction solution containing metformin, 1 to 2 equivalent of acetic acid is preferably used for 1 equivalent of metformin hydrochloride.

In the first and the second steps, an usual solvent is used as a reaction solvent, and preferably, an organic solvent selected from the group consisting of methanol, ethanol, isopropanol, acetone and acetonitrile is used.

The third step is a step of forming a crystalline acid addition salt, and is carried out in a temperature range of −10 to 80° C.

As more simplified process, a method of preparing metformin acetate without performing the first and the second steps is provided. The metformin acetate can be prepared by reacting metformin hydrochloride with an organic alkali under water or an organic solvent condition, and sodium bicarbonate, potassium carbonate and sodium acetate can used as the organic alkali used in preparation process, and sodium acetate is preferably used. Further, as depicted in reaction scheme 2, the metformin acetate can be also prepared by reacting metformin hydrochloride simultaneously with acetic acid and inorganic base, and alkali hydroxide such as sodium hydroxide and potassium hydroxide can be used as the inorganic base used in the preparation process, and sodium hydroxide is preferably used. 1 to 2 equivalents of the organic alkali can be used for 1 equivalent of metformin hydrochloride.

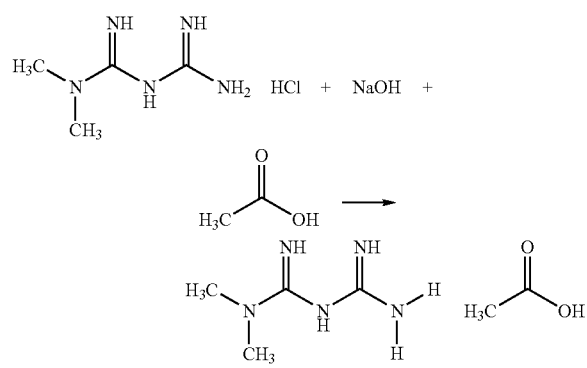

The term metformin acetate herein refers to metformin (1:1) acetate unless mentioned otherwise.

The metformin acetate according to the present invention includes both anhydrous and hydrate, and preferably anhydrous.

According to the present invention, a process for preparing metformin free base was established so that the process could be performed simply and without any special equipment. For removing hydrochloric acid of the metformin hydrochloride, U.S. Pat. No. 4,080,472 uses ion exchange resin column, or U.S. Pat. No. 4,028,402 discloses a preparation method that is carried out under severe conditions of heating to reflux and filtering hot solution. However, the present invention can prepare an organic acid salt of metformin with less cost by simplifying the process so that it can be prepared in general production equipment without any special equipment, thereby rising industrial applicability. The method of preparing this free base can be employed in a reaction with various acids used in preparing a pharmaceutically acceptable salt.

The kind of the pharmaceutically acceptable salt applicable to the method of synthesizing a free base according to the present invention is as follows: hydrochloride, sulfate, nitrate, phosphate, sulfite, dithionate, acetate, benzoate, citrate, glycolate, glyoxylate, mercaptoacetate, γ-hydroxy butyrate, palmoate, aspartate, glutamate, pyrrolidone carboxylate, methane sulfonate, naphthalene sulfonate, glucose-1-phosphate, chlorophenoxy acetate, embonate, chlorophenoxy acetate, maleate, parachlorophenoxy isobutylate, formate, lactate, succinate, tartrate, cyclohexane carboxylate, hexanoate, octanoate, decanoate, hexadecanoate, octodecanoate, benzene sulfonate, trimethoxybenzoate, paratoluene sulfonate, adamantane carboxylate, glutamate, pyrrolidone carboxylate, malonate, malate, oxalate, etc.

Further, the present invention relates to a pharmaceutical composition for treating or preventing diabetes mellitus comprising metformin acetate of the formula 1 as an active ingredient and having various formulations.

The metformin acetate according to the present invention prepared by the above method comprises a pharmaceutically acceptable carrier, and thus can be applied as an oral preparation in various forms, and employed in preparing a pharmaceutical preparation for treating or preventing diabetes mellitus related disease state in the form of a controlled-release and immediately-release tablet, a soft capsule, a hard capsule, a pill, a granule or a powder, an injecting agent and a liquid preparation.

A controlled-release tablet capable of controlling the dissolution rate of a drug among the various oral preparations mentioned above is considered as most preferable administration form, in an aspect that it can prevent drastic change in level in blood and prevent side effects and resistance to a drug, and in consideration of the convenience and treating effect of a patient.

An ingredient selected from an enteric polymer, a hydrophobic compound, and a hydrophilic polymer is used as a matrix agent used for controlled release among the pharmaceutically acceptable carrier. As the enteric polymer, a mixture of at least one or two compound selected from polyvinylacetate phthalate, methacrylic acid copolymer, hydroxypropylmethyl cellulose phthalate, shellac, cellulose acetate phthalate, cellulose propionate phthalate, (poly-(methacrylic acid/methyl-methacrylate) copolymer) can be used, and hydroxypropylmethyl cellulose phthalate is preferably used.

The hydrophobic compound can be selected from pharmaceutically acceptable polyvinyl acetate, poly-methacrylate copolymer, for example, poly-(ethyl acrylate/methyl methacrylate) copolymer, poly-(ethylacrylate/methyl methacrylate/trimethyl amino ethyl methacrylate) copolymer, ethyl cellulose and cellulose acetate, fatty acid and fatty acid ester, fatty acid alcohol, wax and inorganic compound, etc. Specifically, at least one or two compounds can be selected from glyceryl palmitostearate, glyceryl stearate, glyceryl behenate, cetyl palmitate, glyceryl monooleate and stearic acid as fatty acids and fatty acid esters; cetostearyl alcohol, cetyl alcohol and stearyl alcohol as fatty acid alcohols; carnauba wax, bees wax and microcrystalline wax as waxes; talc, precipitated calcium carbonate, dibasic calcium phosphate, zinc oxide, titanium oxide, kaolin, bentonite, montmorillonite and vee gum as inorganic compounds, etc.

Examples of the hydrophilic polymer include, but are not limited to, a saccharide, a cellulose derivative, a gum, a protein, a polyvinyl derivative, a polymethacrylate copolymer, a polyethylene derivative, a carboxyvinyl polymer and a mixture thereof. Specifically, examples of the saccharides include, but are not limited to, dextrin, polydextrin, dextran, pectin and pectin derivative, alginate, poly(galacturonic acid), xylan, arabinoxylan, arabinogalactan, starch, hydroxypropyl starch, amylase, amylopectin and a mixture thereof; examples of the cellulose derivatives include, but are not limited to, hydroxypropylmethyl cellulose, hydroxypropyl cellulose, hydroxymethyl cellulose, hydroxyethyl cellulose, methyl cellulose, carboxymethyl cellulose sodium, hydroxypropyl methyl cellulose acetate succinate, hydroxyethylmethyl cellulose and a mixture thereof; examples of the gums include, but are not limited to, guar gum, locust bean gum, tragacantha, carrageenan, gum acasia, gum arabic, gellan gum, xanthan gum and a mixture thereof; examples of the proteins include, but are not limited to, gelatin, casein, zein and a mixture thereof; examples of the polyvinyl derivatives include, but are not limited to, polyvinyl alcohol, polyvinyl pyrrolidone, polyvinylacetal diethylaminoacetate and a mixture thereof; examples of the polymethacrylate copolymers include, but are not limited to, poly(butyl methacrylate, (2-dimethylaminoethyl)methacrylate, methylmethacrylate) copolymer, poly(methacrylic acid, methylmethacrylate) copolymer, poly(methacrylic acid, ethylacrylate) copolymer and a mixture thereof; examples of the polyethylene derivatives include, but are not limited to, polyethylene glycol, polyethylene oxide and a mixture thereof; and examples of the carboxyvinylpolymers include, but are not limited to, carbomer.

Examples of the pharmaceutically acceptable diluent within a range damaging the effect of the present invention include, but are not limited to, starch, microcrystalline cellulose, lactose, glucose, mannitol, alginate, alkali earth metal salt, clay, polyethylene glycol and dicalcium phosphate, etc. Examples of the binder include, but are not limited to, starch, microcrystalline cellulose, highly dispersive silica, mannitol, lactose, polyethylene glycol, polyvinyl pyrrolidone, hydroxypropyl methylcellulose, hydroxypropyl cellulose, natural gum, synthetic gum, copovidone and gelatin, etc. Examples of the disintegrant include, but are not limited to, starch or denatured starch, for example, sodium starch glycolate, corn starch, potato starch or pre-gelatinized starch, etc; clay, for example, bentonite, montmorilonite and veegum, etc.; cellulose, for example, microcrystalline cellulose, hydroxylpropyl cellulose or carboxymethyl cellulose, etc.; algin, for example, sodium alginate or alginic acid; crosslinked cellulose, for example, croscarmellose sodium, etc.; gum, for example, guar gum and xanthan gum, etc.; crosslinked polymer, for example, crospovidone; effervescent preparation, for example, sodium bicarbonate and citric acid, etc. Examples of the lubricant include, but are not limited to, talc, magnesium stearate, alkali earth metal stearate calcium, zinc, lauryl sulfate, hydrogenated vegetable oil, sodium benzoate, sodium stearyl fumarate, glyceryl monostearate and polyethylene glycol 4000.

The scope of the present invention is not limited to using the excipient, and the excipient can be contained in a usual content range by a person skilled in the art.

As described above, the metformin acetate can be applied as various forms of a preparation for oral administration, and a dosage of the pharmaceutical composition according to the present invention to a human body can vary depending on a patient's age, gender, body weight, nationality, health state and disease state and divisional administration is also possible pursuant to discretion of a physician.

The present invention will be described in greater detail with reference to the following examples. The following examples are for illustrative purposes only and are not intended to limit the scope of the invention.

Example 1

Preparation of Metformin Acetate 2 kg (1 equivalent) of metformin hydrochloride and 483 g (1 equivalent) of sodium hydroxide were stirred in 10 L of methanol for 2 hours at room temperature, and then remaining solid was filtered and the filtrate was concentrated under reduced pressure. Then 15 L of acetone was added to the resulting solid and stirred. Insoluble material was filtered, and the filtrate was concentrated under reduced pressure to obtain 1,230 g of metformin free base. The metformin free base was dissolved in 33 L of acetone, 2.8 L (4 equivalents) of acetic acid was added, and then the mixture was stirred for 2 hours at room temperature. The resulting crystal was filtered, and re-crystallized in water and acetone to obtain 1,089 g of metformin acetate (yield: 47.7%).

Example 2

Preparation of Metformin Acetate

5 L of water, 2 kg (1 equivalent) of metformin hydrochloride and 578 g (1.2 equivalents) of sodium hydroxide were added to 10 L reactor, and stirred for 2 hours at room temperature. Then 1 L (1.45 equivalents) of acetic acid was added for 1 hour, and the mixture was stirred overnight at room temperature. The resulting crystal was washed with acetone-water (12:1) mixture, and then acetone, and dried at 60° C. to obtain 1,112 g of metformin acetate (yield: 48.7%).

Example 3

Preparation of Metformin Acetate

1 Kg (1 equivalent) of metformin hydrochloride and 2 L of water, and then 0.5 L (1.45 equivalents) of acetic acid were added to a reactor, and stirred for 2 hours at 30° C. to dissolve thoroughly. Then 289.8 g (1.2 equivalents) of aqueous solution of sodium hydroxide were added to the reaction solution for 1 hour. The resulting crystal was filtered and washed with acetone, and then dried at 60° C. to obtain 601 g of metformin acetate (yield: 52.7%).

Example 4

Preparation of Metformin Acetate 20.0 g (1 equivalent) of metformin hydrochloride and 30 Ml of water, and then 10 Ml (1.45 equivalents) of acetic acid were added to a reactor, and stirred for 2 hours at 30° C. to dissolve thoroughly. Then 1.23 g (1.5 equivalents) of aqueous solution of sodium hydroxide was added to the reaction solution. The resulting crystal was filtered and washed with acetone, and then dried at 60° C. to obtain 16.7 g of metformin acetate (yield: 73.0%).

Example 5

Preparation of Metformin Acetate 20.0 g (1 equivalent) of metformin hydrochloride, 50 Ml of water, and 19.72 g (1.2 equivalents) of sodium acetate trihydrate were added to a reactor, and stirred. Then the resulting crystal was filtered and washed with acetone, and then dried at 60° C. to obtain 11.72 g of metformin acetate (yield: 51.3%).

Example 6

Preparation of Metformin Acetate 0.4 L of water, 241.50 g of sodium hydroxide, 9 L of acetone and 1 Kg of metformin hydrochloride were added to a 20 L reactor, and stirred for 2 hours and 40 minutes at room temperature. The resulting crystal was filtered and washed with acetone. 0.2 L of water and 1 L of acetic acid were added and stirred. The resulting crystal was filtered and washed with acetone, and then dried at 60° C. to obtain 1,056 g of metformin acetate (yield: 92.4%).

Example 7

Preparation of Metformin Acetate 78 g (1 equivalent) of metformin free base, 234 Ml of isopropanol, 234 Ml of water and 57 Ml (1.65 equivalents) of acetic acid were added to a reactor, and stirred. The resulting crystal was filtered and washed with isopropanol, and then dried at 60° C. to obtain 54.6 g of metformin acetate (yield: 47.8%).

Example 8

Preparation of Metformin Acetate 20.00 g (1 equivalent) of metformin hydrochloride and 4.84 g (1 equivalent) of sodium hydroxide were stirred in 200 Ml of ethanol for 2 hours at room temperature, and then remaining solid was filtered and the filtrate was concentrated under reduced pressure. Then 300 Ml of acetone was added to the resulting solid and stirred. Insoluble material was filtered, and the filtrate was concentrated under reduced pressure to obtain 12.0 g of metformin free base. 500 Ml of acetone and 10 Ml (1.45 equivalents) of glacial acetic acid were added to the metformin free base, and then the mixture was stirred. The resulting crystal was filtered and washed with acetone, and then dried at 60° C. to obtain 13.6 g of metformin acetate (yield: 59.5%).

Example 9

Preparation of Metformin Acetate 20.0 g (1 equivalent) of metformin hydrochloride and 50 Ml of water, and then 10 Ml (1.45 equivalents) of glacial acetic acid were added to a reactor, and stirred for 2 hours at 30° C. to dissolve thoroughly. Then 10.2 g (1.5 equivalents) of aqueous solution of potassium hydroxide were added to the reaction solution. The resulting crystal was filtered and washed with acetone, and then dried at 60° C. to obtain 13.3 g of metformin acetate (yield: 58.2%).

Example 10

Pharmaceutical Composition of Metformin Acetate

Metformin acetate, hydroxypropyl methyl cellulose and light anhydrous silicic acid were poured with the content as indicated in Table 2 below and mixed, and then roller compacted under a pressure of 16 to 17 MPa to give slug. The resulting slug was granulated with No. 14 size, magnesium stearate was mixed, and the mixture was compressed to prepare a tablet layer. Then a film-coated layer was formed with Opadry OY-C-7000A as a coating agent using Hi-Coater (SFC-30N, Sejong Machine Co., Ltd, Korea) to prepare a metformin controlled release tablet containing 500 mg of metformin acetate.

Example 11

Pharmaceutical Composition of Metformin Acetate

Metformin acetate, carboxymethyl cellulose sodium, microcrystalline cellulose and light anhydrous silicic acid were poured with the content as indicated in Table 2 below and mixed, and then roller compacted under a pressure of 16 to 17 Mpa to give slug. The resulting slug was granulated with No. 14 size, magnesium stearate was mixed, and the mixture was compressed to prepare a tablet. Then a film-coated tablet was formed with Opadry OY-C-7000A as a coating agent using Hi-Coater (SFC-30N, Sejong Machine Co., Ltd, Korea) to prepare a metformin controlled release tablet containing 500 mg of metformin acetate.

Example 12

Pharmaceutical Composition of Metformin Acetate

Metformin acetate, polyvinyl pyrrolidone, hydroxypropyl methyl cellulose and glyceryl behenate were poured with the content as indicated in Table 2 below with No. 20 size and mixed. Light anhydrous silicic acid was screened with No. 35 size, magnesium stearate was mixed, and the mixture was compressed to prepare a tablet layer. Then a film-coated layer was formed with Opadry OY-C-7000A as a coating agent using Hi-Coater (SFC-30N, Sejong Machine Co., Ltd, Korea) to prepare a metformin controlled release tablet containing 750 mg of metformin acetate.

Comparative Example 1

Preparation of Metformin Hydrochloride 500 mg of metformin free base was dissolved in 30 Ml of acetone, and then 280 Ml of concentrated hydrochloric acid was added, and stirred for 2 hours at room temperature. The resulting crystal was filtered and washed with acetone, and then dried with heated air at 70° C. to obtain 490 mg of metformin hydrochloride (yield: 76.4%).

Comparative Example 2

Pharmaceutical Composition of Metformin Hydrochloride

Metformin hydrochloride, hydroxypropyl methyl cellulose and light anhydrous silicic acid were poured with the content as indicated in Table 2 below and mixed, and then roller compacted under a pressure of 16 to 17 MPa to give slug. The slug was granulated with No. 14 Size, magnesium stearate was mixed, and the mixture was compressed to prepare a tablet. Then a film-coated tablet was formed with Opadry OY-C-7000A as a coating agent using Hi-Coater (SFC-30N, Sejong Machine Co., Ltd, Korea) to prepare a metformin controlled release tablet containing 500 mg of metformin hydrochloride.

Comparative Example 3

Pharmaceutical Composition of Metformin Hydrochloride

Metformin hydrochloride, carboxymethyl cellulose sodium, microcrystalline cellulose and light anhydrous silicic acid were poured with the content as indicated in Table 2 below and mixed, and then roller compacted under a pressure of 16 to 17 MPa to give slug. The slug was granulated with No. 14 Size, magnesium stearate was mixed, and the mixture was compressed to prepare a tablet. Then a film-coated tablet was formed with Opadry OY-C-7000A as a coating agent using Hi-Coater (SFC-30N, Sejong Machine Co., Ltd, Korea)

to prepare 500 mg of a metformin controlled release tablet containing 500 mg of metformin hydrochloride.

Comparative Example 4

Pharmaceutical Composition of Metformin Hydrochloride

Metformin hydrochloride, polyvinyl pyrrolidone, hydroxypropyl methyl cellulose and glyceryl behenate were poured with the content as indicated in Table 2 below with No. 20 size and mixed. Light anhydrous silicic acid was granulated with No. 35 size, magnesium stearate was mixed, and the mixture was compressed to prepare a tablet layer. Then a film-coated layer was formed with Opadry OY-C-7000A as a coating agent using Hi-Coater (SFC-30N, Sejong Machine Co., Ltd, Korea) to prepare a metformin controlled release tablet containing 750 mg of metformin hydrochloride.

TABLE 2

| | | Component ratio (mg/tablet) | | | | | |
| | | Example | | | Comparative example | | |
| Ingredient | | 10 | 11 | 12 | 2 | 3 | 4 |
|---|---|---|---|---|---|---|---|
| Main ingredient | Metformin acetate | 500 | 500 | 750 | | | |
| | Metformin hydrochloride | | | | 500 | 500 | 750 |
| Excipient | Polyvinyl pyrrolidone | | 120 | | | 120 | |
| | Hydroxypropyl methyl cellulose | 500 | | 240 | 500 | | 240 |
| | Carboxymethyl cellulose sodium | | 450 | | | 450 | |
| | Avicel PH101 | | 41 | | | 41 | |
| | Glyceryl behenate | | | 30 | | | 30 |
| | Aerosil 200 | 5 | 5 | 7.5 | 5 | 5 | 7.5 |
| | Magnesium stearate | 5 | 4 | 7.5 | 5 | 4 | 7.5 |
| Coating agent | Opadry OY-C-7000A | 40 | 40 | 60 | 40 | 40 | 60 |
| Total | | 1050 | 1040 | 1215 | 1050 | 1040 | 1215 |

Experimental Example 1

Qualitative Confirmation for the Structure of Metformin Acetate

From X-ray diffraction spectrum, nuclear magnetic resonance spectrum data, infrared spectrum data and melting point for metformin acetate of the formula 1 prepared by Example 1, it was confirmed that metformin acetate according to the present invention has different crystal form and structure from metformin hydrochloride of the formula 4 prepared by Comparative example 1.

1) Powder X-Ray Diffraction Analysis Spectrum

Figure 2:
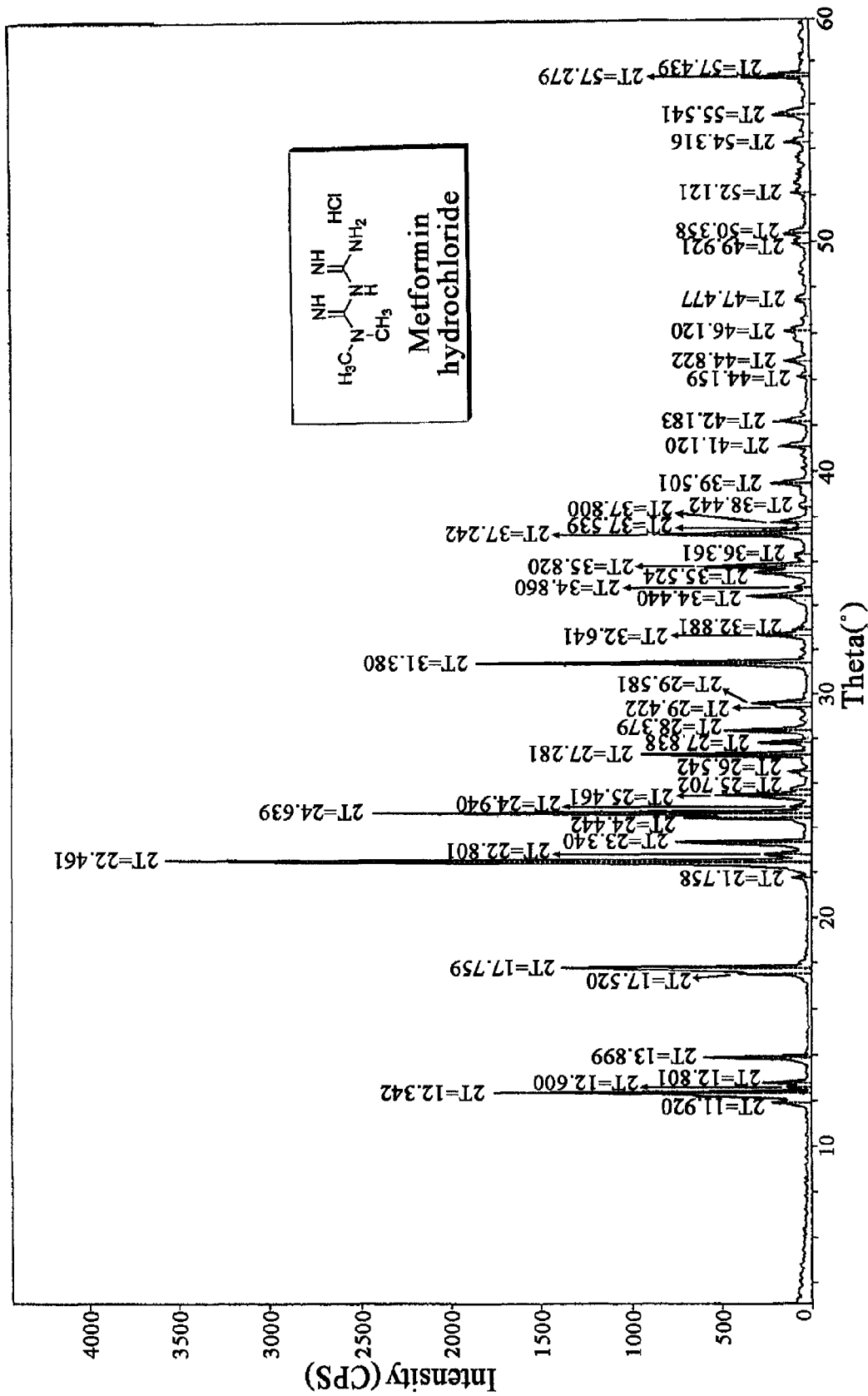
FIG. 2 is the result of XRD measurement for metformin hydrochloride of Comparative example 1.

The characteristic peak for metformin acetate shown in powder X-ray diffraction analysis spectrum depicted in FIG. 1 is indicated in Table 3 below. Here "2θ" means a diffraction angle, "d" means the distance between crystal faces, "I/Io" means the relative strength of a peak. The following analysis was performed by D/MAX-2200V X-ray Diffractometer (XRD) available at Rigaku Company. From comparison of metformin acetate shown in FIG. 1 with metformin hydrochloride shown in FIG. 2, it was confirmed that a different crystal was obtained.

TABLE 3

| 2θ | d | I/Io |
|---|---|---|
| 11.940 | 7.4063 | 223 |
| 15.740 | 5.6257 | 318 |
| 17.699 | 5.0070 | 1000 |
| 19.281 | 4.5997 | 618 |
| 20.231 | 4.3666 | 595 |
| 21.399 | 4.1489 | 213 |
| 21.819 | 4.0699 | 157 |
| 24.040 | 3.6988 | 649 |
| 26.280 | 3.3884 | 501 |
| 27.839 | 3.2020 | 407 |
| 28.540 | 3.1250 | 670 |
| 29.920 | 2.9839 | 251 |
| 33.480 | 2.6743 | 109 |
| 35.580 | 2.5211 | 102 |

2) Measurement of Melting Point

It was confirmed that metformin acetate of the formula 1 prepared in Example 1 has a melting point of 227.3~228.0□, metformin hydrochloride of Comparative example 1 has a melting point of 222.8~224.0□.

3) Elemental Analysis

From the elemental analysis for metformin acetate of the formula 1 prepared in Example 1, it was confirmed that 1 equivalent of acetic acid is bound in the metformin acetate when comparing actual measurement values with the theoretical values of a monovalent salt and a divalent salt. The analysis results as shown in Table 4 were obtained by FISONS EA-1108 Elemental Analyzer for C, H and N, and Thermo Finnegan FLASH EA-1112 Elemental Analyzer for O.

TABLE 4

| Analysis item | C (%) | H (%) | N (%) | O (%) |
|---|---|---|---|---|
| Measurement value of metformin acetate | 38.2 | 8.2 | 36.8 | 17.0 |
| Theoretical value of metformin monoacetate | 38.09 | 7.99 | 37.01 | 16.91 |
| Theoretical value of metformin diacetate | 38.55 | 7.68 | 28.10 | 25.67 |

4) Data for Nuclear Magnetic Resonance Spectrum (NMR)

Figure 3:
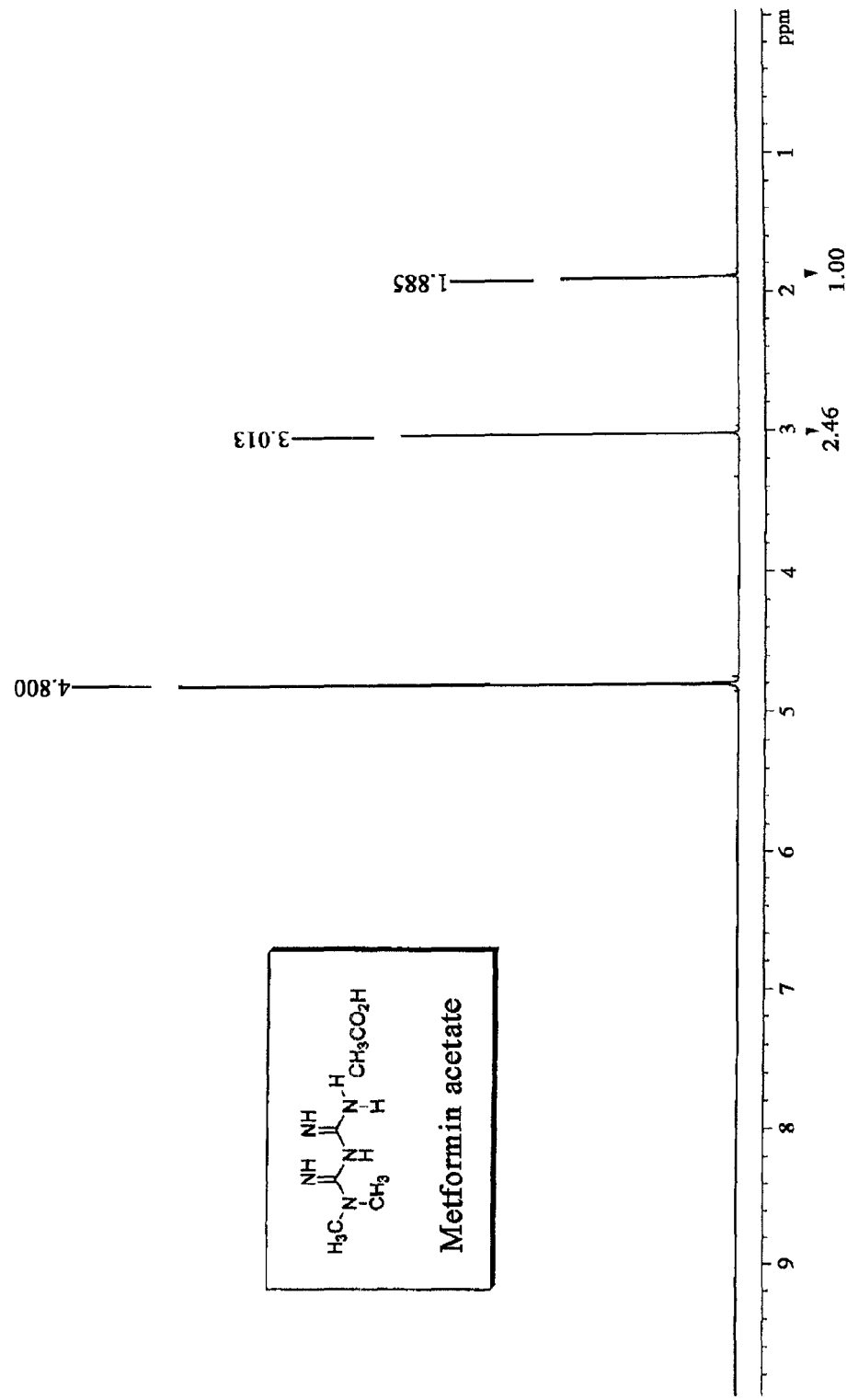
FIG. 3 is the result of NMR measurement for metformin acetate of Example 1 according to the present invention.
Figure 4:
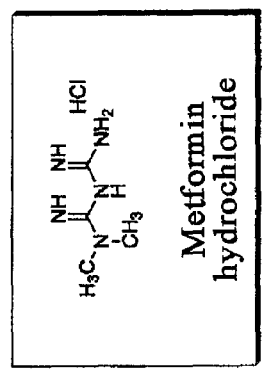
FIG. 4 is the result of NMR measurement for metformin hydrochloride of Comparative example 1.
Figure 4:
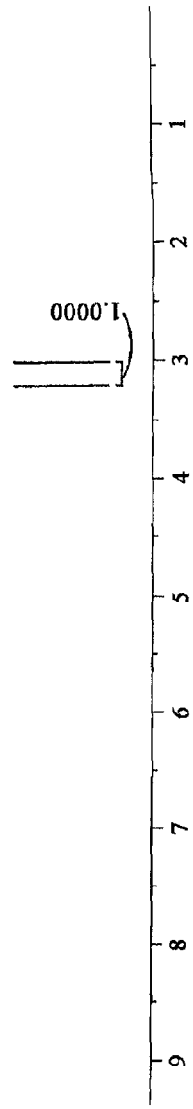

By confirming the peak of nuclear magnetic resonance (1H-NMR) for metformin acetate of the formula 1 prepared in Example 1 (FIG. 3) and the peak of metformin hydrochloride of Comparative example 1 (FIG. 4), it could be found that acetic acid is bound to metformin free base since it was confirmed that the methyl group of acetic acid was generated in δ=1.885 ppm.

5) Data for Infrared Spectroscopy (FT-IR)

Figure 5:
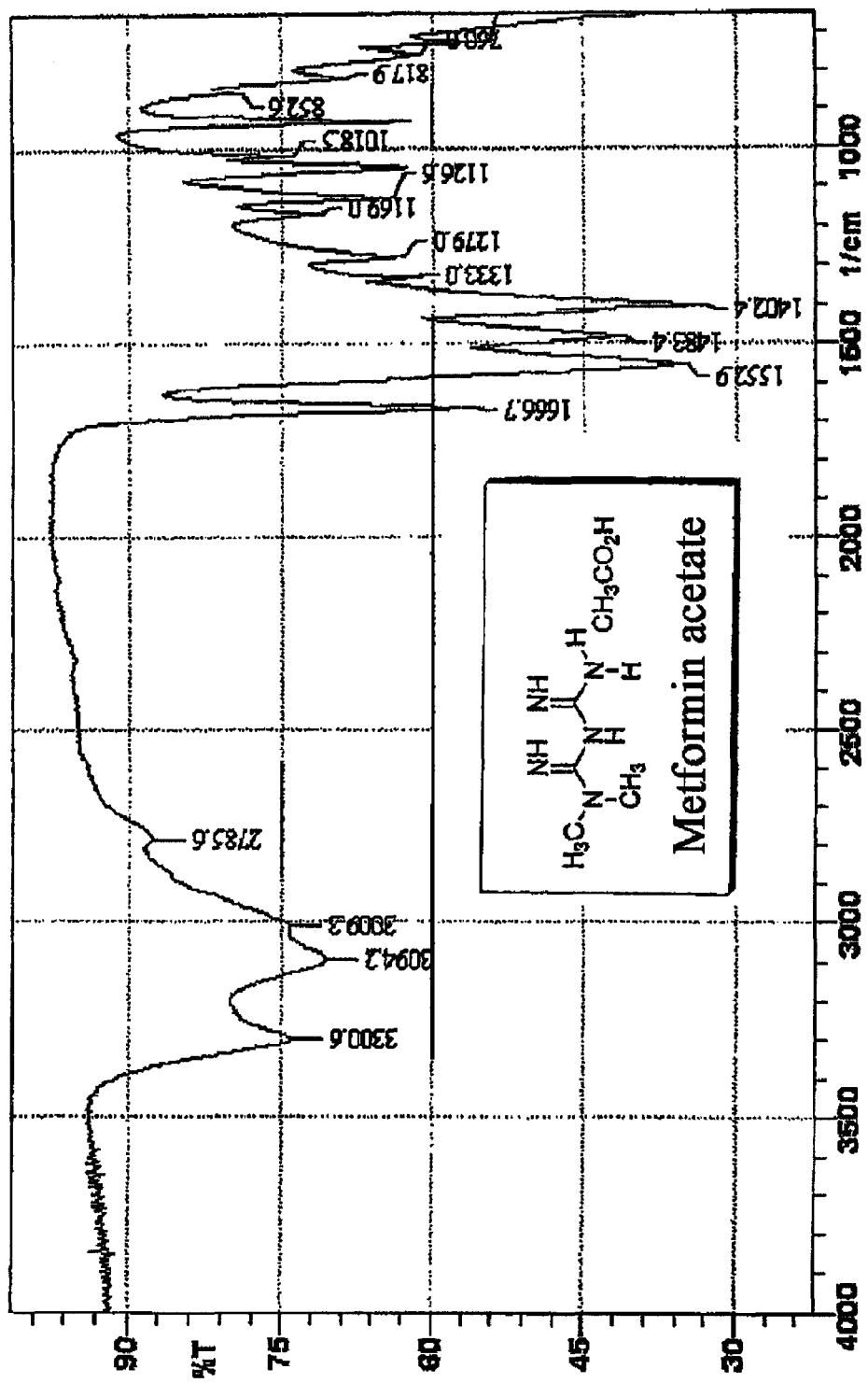
FIG. 5 is the result of IR measurement for metformin acetate of Example 1 according to the present invention.
Figure 6:
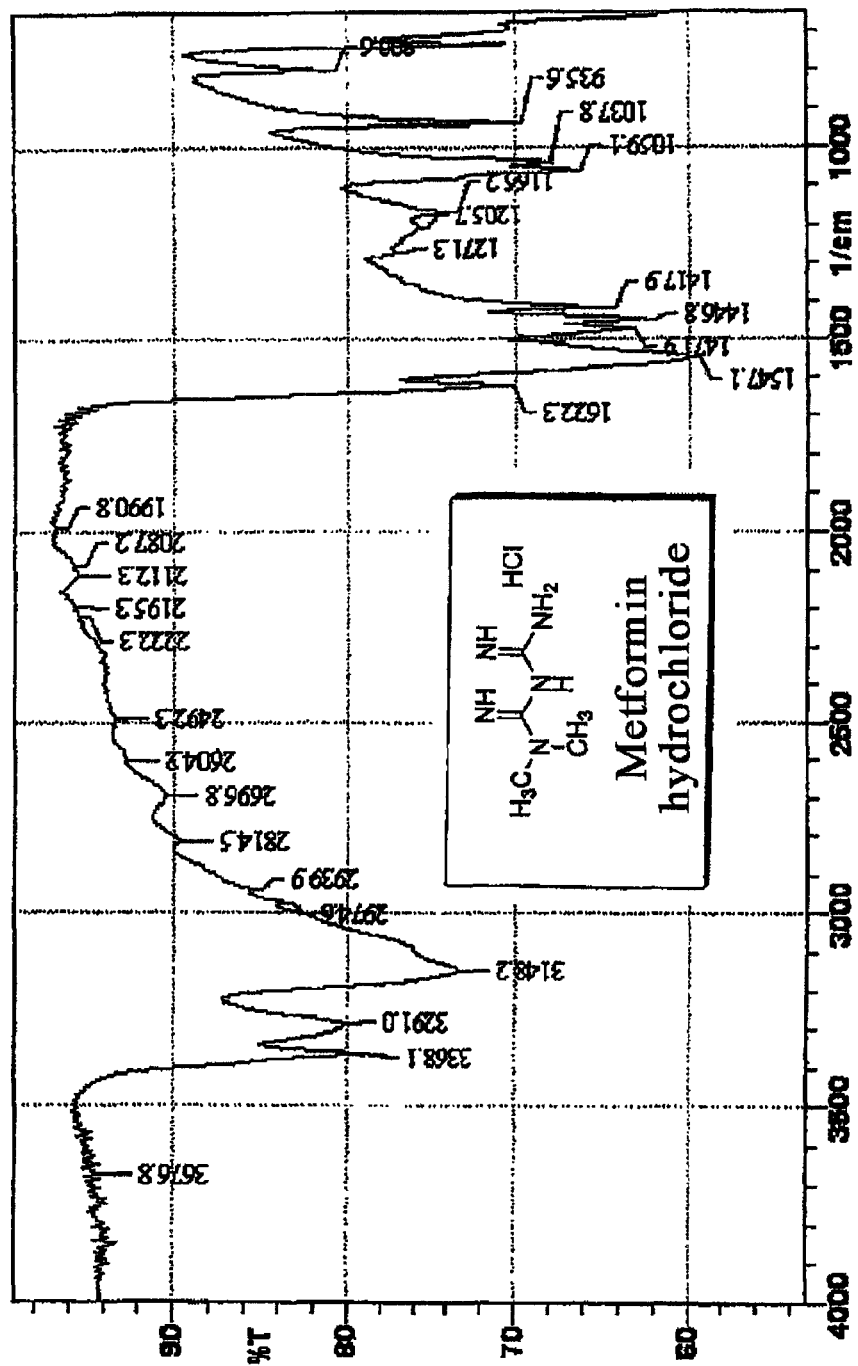
FIG. 6 is the result of IR measurement for metformin hydrochloride of Comparative example 1.
Figure 7:
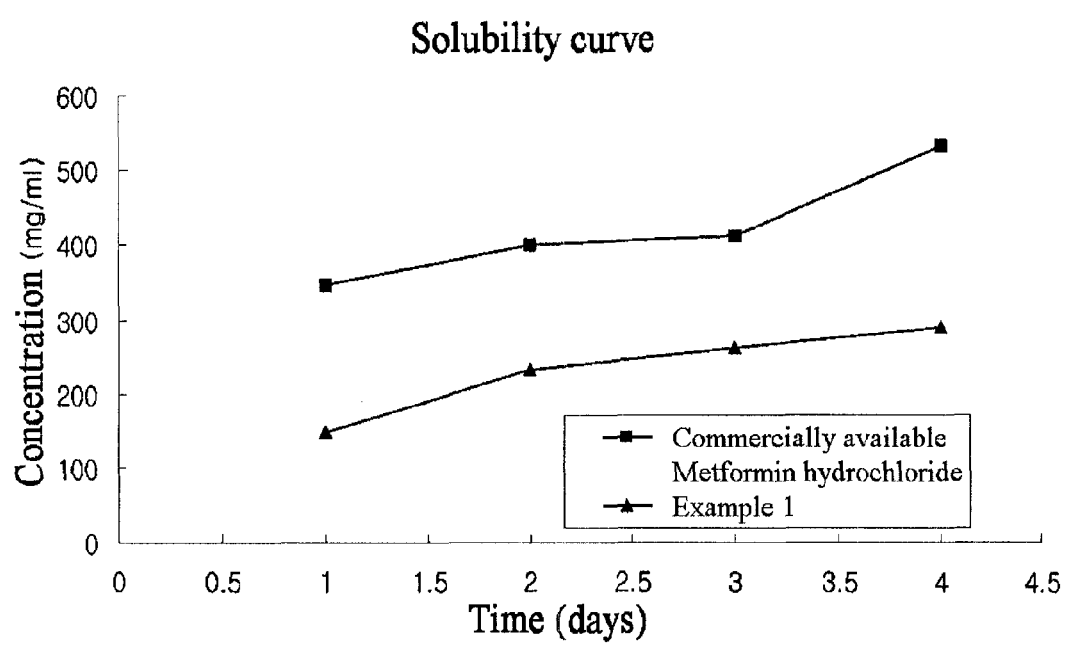
FIG. 7 is the result of solubility measurement for Experimental example 2 according to the present invention.
Figure 8:
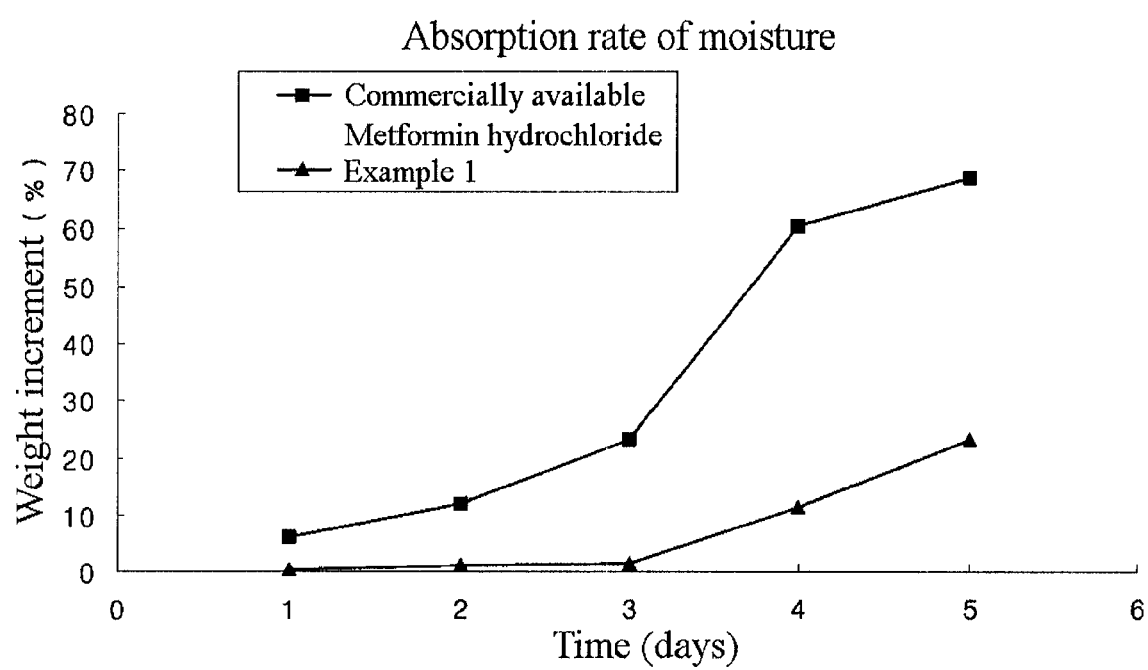
FIG. 8 is the result of hygroscopicity measurement for Experimental example 3 according to the present invention.

By confirming the peak of infrared spectroscopy (FT-IR) for metformin acetate of the formula 1 prepared in Example 1 (FIG. 5) and the peak of metformin hydrochloride of Comparative example 1 (FIG. 6), it could be found that acetic acid is bound to metformin free base since peaks were totally changed, and in particular, the carbonyl group of acetic acid was generated at 1622 cm-1.

Experimental Example 2

Measurement of Solubility in Water

The solubility of the Metformin acetate of the formula 1 prepared in Example 1 in water were compared with that of the metformin hydrochloride employed as an active ingredient of metformin pharmaceutical composition.

The condition and method of experiment is as follows.

1) Water was filled in an agitated water bath, and its temperature was set as 30□.

2) 20 mL of water was filled in 100 mL Erlenmeyer flask, and 10 g of metformin hydrochloride and metformin hydrochloride were poured thereto, respectively.

3) The Erlenmeyer flasks containing the metformin acetate and the metformin hydrochloride, respectively, were fixed to the rack of the water bath, and then the apparatus was operated with a speed of 60 times per minute at 30□.

4) Samples were taken and filtered with an interval of 24 hours, and then their concentration was calculated by quantitative analysis with an ultraviolet spectrophotometer ($\lambda$=233 nm).

The above experimental procedures were repeated for 5 days, and the saturation solubility at 30□ and the velocity reaching the saturation solubility were obtained and indicated in Table 5 below.

TABLE 5

| | Saturation solubility (mg/ml) | Concentration according to the time in Shaking Water Bath (30° C.) (mg/ml) | | | |
|---|---|---|---|---|---|
| | | 1 day | 2 days | 3 days | 5 days |
| Metformin hydrochloride | 440 | 347.66 | 400.25 | 412.36 | 534.61 |
| Metformin acetate | 280 | 148.51 | 233.76 | 261.66 | 292.48 |

As shown in the Table 5, from measurement of each saturation solubility of the metformin acetate and the metformin hydrochloride after 5 days, it can be seen that the saturation solubilites are 292.48 mg/mL, and 534.61 mg/mL, respectively, indicating that the solubility of the acetate is lower than that of the hydrochloride. As shown in the Table 5, the metformin acetate has lower saturation solubility than that of the metformin hydrochloride, as well as has the speed reaching the saturation solubility slower than that of the hydrochloride. Therefore, the metformin acetate is advantageous in formulating since desired release rate can be achieved by using less polymeric excipient in preparing a controlled release tablet of metformin.

Experimental Example 3

Measurement of Hygroscopicity

The hygroscopicities of the metformin acetate of the formula 1 prepared in Example 1 and commercially available metformin hydrochloride employed as an active ingredient of metformin pharmaceutical composition were compared.

The experimental condition and method are as follows.

1) Metformin hydrochloride and metformin acetate were dried at 40□ for 24 hours, respectively, to reach constant amounts.

2) Saturated solution of $KH_2PO_4$ (22 g/100 g) was filled in the bottom of a desiccator, and the inner humidity was set to 95% and the temperature of the desiccator located room was maintained as 25° C.

3) 100 mg of metformin hydrochloride and metformin acetate were precisely taken, respectively and their weights were measured together with a container.

4) Metformin hydrochloride and metformin acetate were filled in the desiccator together with the container, and picked up together in the interval of 24 hours with the container, and their weights were measured and it was calculated that moisture was absorbed by the increment in weight.

After repeating the above experimental procedure for 6 days, the hygroscopicity at 95% RH, 25° C. was as indicated in Table 6 below.

TABLE 6

| | Hygroscopicity (%) | | | | |
|---|---|---|---|---|---|
| | 1 day | 2 days | 3 days | 6 days | 9 days |
| Metformin hydrochloride | 6.29 | 11.86 | 23.3 | 60.33 | 68.78 |
| Metformin acetate | 0.35 | 0.93 | 1.37 | 11.21 | 23.32 |

As indicated in the Table 6, the hygroscopicity of the metformin acetate was lower than that of the metformin hydrochloride.

The metformin hydrochloride absorbs moisture during transport and its particles are compressed each other to form aggregates due to its high hygroscopicity, but the metformin acetate can decrease greatly the possibility of changing its status during transport, and can show excellent fluidity without forming aggregates in pharmaceutical preparation steps such as compression step for long period for preparing a product.

Experimental Example 4

Confirmation Test of pKa (Spectrographic Analysis)

Figure 9:
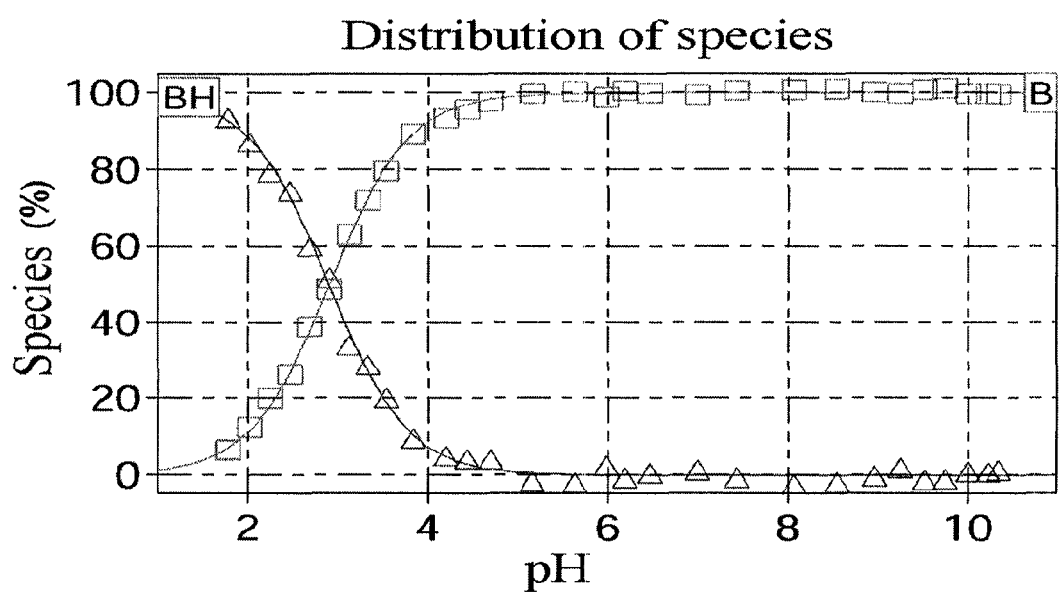
FIG. 9 is the result of pKa measurement for metformin acetate according to the present invention.

The ionized metformin acetate of the formula 1 prepared in Example 1 acts as an acid, a free base or an amphipathic compound depending on pH, thereby generating the pH change at each titration point. Thus, pKa value was obtained from the difference between the calculated pH value and actually measured pH value. The pKa value is indicated in Table 7 below, and its result was depicted in FIG. 9.

TABLE 7

| | pKa | Error |
|---|---|---|
| Metformin acetate | 2.853 | ±0.010 |

Experimental 5

Figure 10:
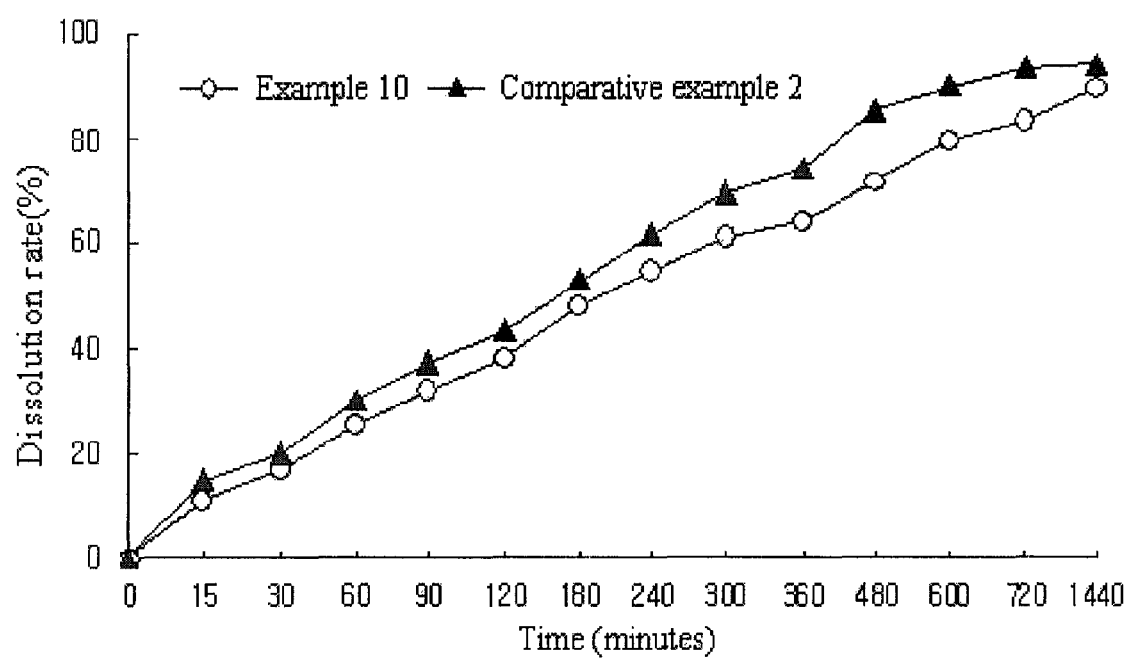
FIG. 10 is the result of dissolution measurement for the controlled release tablet of metformin acetate of Example 10 according to the present invention and the controlled release tablet of metformin acetate prepared by Comparative example 2.

Comparative Dissolution Profile Test Between Metformin Acetate and Metformin Hydrochloride Dissolution property by paddle method in dissolution test among general tests in the Korean Pharmacopoeia was measured by using the controlled release tablet of the metformin acetate according to the present invention prepared by Example 10 and the controlled release tablet of the metformin hydrochloride prepared by Comparative example 2, and the results are shown in FIG. 10.

From the experimental results, when comparing the dissolution properties of the controlled release tablet of the metformin acetate designed as all the same preparations except that an active ingredient is different, and the controlled release tablet of metformin hydrochloride, it can be found that the metformin acetate shows lower and extended dissolution rate by the difference in solubility.

Experimental Example 6

Comparative Efficacy Test Between Metformin Acetate and Metformin Hydrochloride

1. Effect of Drop in Blood Glucose Level

This test supports the effect of the present invention. In this test, the metformin acetate of Example 1 and commercially available metformin hydrochloride were administered to an experimental animal, and the procedure described in Table 8 below was performed in order to compare their effects.

TABLE 8

| | |
|---|---|
| Subject | Comparative test for the effects of drop in blood glucose for metformin acetate and metformin hydrochloride |
| Purpose | Compare the effects of drop in blood glucose by administering metformin acetate and metformin hydrochloride to diabetes mellitus induced experimental animal |
| Test subject | 210 to 230 g of male rats aged 8 weeks |
| Test method | 1) Select rats that was judged as healthy during acclimatizing period for 5 days.<br>2) Induce diabetes mellitus in the rats by injecting alloxan (40 mg/kg) intravenously twice with an interval of 48 hours.<br>3) Select an individual having at least 13.8 mmol/L of glucose and divide into three groups 6 days after administration of alloxan.<br>4) Administer a saline group (control group; n = 5), metformin hydrochloride (0.05 mg corresponding amount as metformin active ingredient; n = 5), metformin acetate (0.05 mg corresponding amount as metformin inductive ingredient; n = 5) peritoneally to each group. After administration, the glucose concentration in blood was confirmed for 10 hours. |
| Evaluation method | [Measurement of glucose concentration]<br>1) After administration of a drug, the glucose concentration in blood was measured at 0, 2, 4, 6, 8, 10 hours.<br>2) Taking blood of tail vein at each time frame to measure the glucose concentration in blood with a blood glucose level. |

The detailed results of the test for drop in blood glucose are indicated in Table 9 below.

TABLE 9

| | Glucose concentration in blood, mmol/L | | |
|---|---|---|---|
| Hours | Metformin hydrochloride | Metformin acetate | Control group |
| 0 | 13.8 | 13.8 | 13.8 |
| 2 | 7.8 | 6.4 | 14.4 |
| 4 | 6.4 | 7.5 | 14.2 |
| 6 | 8.6 | 6.8 | 14.5 |
| 8 | 7.9 | 5.9 | 14.8 |
| 10 | 9.4 | 6.9 | 14.4 |

As indicated in the Table 9, the glucose concentration 10 hours after administration of control group was 14.4 mmol/L. The glucose concentration 10 hours after administration of metformin acetate administered group was 6.9 mmol/L, indicating the decrease of about 7.5 mmol/L. Meanwhile, the blood glucose concentration in blood 10 hours after administration of metformin hydrochloride administered group was 9.4 mmol/L, indicating lower glucose concentration in blood than that of the control group, but higher glucose concentration in blood than that of the metformin acetate. In other words, it was confirmed that the effect of drop in blood glucose of metformin acetate is more excellent than that of metformin hydrochloride.

2. Test of Drop in Blood Glucose after Meal

This test supports the effect of the present invention. In this test, the metformin acetate of Example 1 and commercially available metformin hydrochloride were administered to an experimental animal, and the procedure described in Table 10 below was performed in order to compare their effects.

TABLE 10

| | |
|---|---|
| Subject | OGTT of metformin acetate and metformin hydrochloride |
| Purpose | Compare the effects of drop in blood glucose after meal for metformin acetate and metformin hydrochloride |
| Test subject | 26~28 g of male ICR mice aged 5 weeks |
| Test method | 1) Select mice that was judged as healthy during acclimatizing period.<br>2) Fast the mice for 12 hours before test, and then divide into eight groups.<br>3) Test groups were set as follows.<br><br>| Test group | Animal (number) | Administration path |<br>|---|---|---|<br>| G1: No treating control group | 8 | Oral |<br>| G2: 100 mg/kg of metformin acetate | | |<br>| G3: 200 mg/kg of metformin acetate | | |<br>| G4: 400 mg/kg of metformin acetate | | |<br>| G5: 100 mg/kg of metformin hydrochloride | | |<br>| G6: 200 mg/kg of metformin hydrochloride | | |<br>| G7: 400 mg/kg of metformin hydrochloride | | |<br>| G8: Excipient control group | | |<br><br>4) 2 g/kg of sucrose was administered orally to G2 to G8 1 hour after administering test material to each group.<br>5) The glucose concentration in blood was confirmed for 4 hours after administration of sucrose. |
| Evaluation method | [Measurement of glucose concentration]<br>1) After administration of sucrose, the glucose concentration in blood was measured at 20, 40, 60, 90, 120, 240 minutes.<br>2) Taking blood of tail vein at each time frame to measure the glucose concentration in blood with a blood glucose level. |

The detailed results of the test for drop in blood glucose after meal are indicated in Table 11 below.

TABLE 11

| <Unit: mg/dl> | | | | | | | |
|---|---|---|---|---|---|---|---|
| Group | 0 min | 20 min | 40 min | 60 min | 90 min | 120 min | 240 min |
| G1 | 113.00 ± 2.64 | 105.25 ± 4.16** | 115.13 ± 4.08* | 122.75 ± 4.88** | 113.38 ± 5.85 | 114.88 ± 5.59 | 77.00 ± 3.55 |
| G2 | 101.63 ± 4.94 | 262.13 ± 15.33** | 212.00 ± 15.68 | 170.75 ± 17.38 | 134.50 ± 15.64 | 106.63 ± 10.44 | 63.63 ± 4.94 |
| G3 | 101.63 ± 4.58 | 213.13 ± 11.36** | 201.00 ± 21.78 | 165.75 ± 15.91 | 129.63 ± 8.08 | 106.38 ± 4.07 | 80.00 ± 3.73 |
| G4 | 104.13 ± 6.53 | 190.25 ± 16.05** | 169.63 ± 21.19 | 141.50 ± 18.24* | 106.38 ± 13.75 | 86.25 ± 11.25** | 69.25 ± 7.96 |
| G5 | 104.00 ± 6.53 | 246.00 ± 16.70** | 194.38 ± 8.02 | 151.50 ± 5.45* | 122.38 ± 4.69 | 111.75 ± 6.45 | 83.63 ± 3.49 |
| G6 | 107.13 ± 2.84 | 227.50 ± 20.57** | 187.25 ± 15.16 | 147.25 ± 9.89* | 121.25 ± 8.15 | 106.75 ± 5.65 | 87.13 ± 4.50 |

TABLE 11-continued

<Unit: mg/dl>

| Group | 0 min | 20 min | 40 min | 60 min | 90 min | 120 min | 240 min |
|---|---|---|---|---|---|---|---|
| G7 | 104.75 ± 3.98 | 187.38 ± 10.32** | 167.63 ± 7.04 | 135.63 ± 5.53** | 110.50 ± 4.78 | 87.88 ± 9.90** | 64.38 ± 7.69 |
| G8 | 106.13 ± 4.06 | 337.88 ± 24.06 | 260.00 ± 26.29 | 198.75 ± 22.16 | 156.38 ± 18.83 | 131.00 ± 17.11 | 81.00 ± 6.48 |

*Remarkably different with G8, $P < 0.05$
**Remarkably different with G8, $P < 0.01$ 1) The effect of drop in blood glucose could be observed in G3, G4, G6 and G7 compared to G8 at 20 minutes after administration of sucrose.
2) The effect of drop in blood glucose could be observed in G3 at 120 minutes, and in G2 and G3 at 240 minutes.
3) It could be found that the metformin acetate showed higher effect of drop in blood glucose than that of the metformin hydrochloride in 200 and 400 mg/kg dosage group at 20 to 60 minutes after administration of sucrose.
4) From the results, it could be inferred that the effect of drop in blood glucose after meal of the metformin acetate was more excellent than that of the metformin hydrochloride.

INDUSTRIAL APPLICABILITY

As described above, metformin acetate according to the present invention is excellent in the effect of drop in blood glucose compared to the previous metformin hydrochloride, and in particular, is remarkably excellent in the effect of drop in blood glucose after meal compared to the metformin hydrochloride having weak ability of controlling blood glucose after meal. Further, the present invention enhanced industrial applicability so that a novel salt of the metformin can be synthesized with less cost by improving the steps simply so that the synthesis can be performed in general production equipment without special equipment compared to the previous preparation method that was difficult to perform or must be performed under severe condition. Further, since metformin acetate has lower solubility than that of the metformin hydrochloride, excessive drop in blood glucose and quick loss of a drug due to drastic release can be prevented. Therefore, the metformin acetate is very useful as an active ingredient of a pharmaceutical since it is formulated in immediate release form or controlled release form for 24 hours a day, and thus it is easy to maintain equal concentration in blood.

The invention claimed is:

1. A method of preparing the metformin acetate of formula 1, which comprises reacting the metformin hydrochloride of formula 4 in alcohol with inorganic base to generate metformin free base; removing the resulting inorganic salt through filtering and concentrating process; and reacting the resultant with acetic acid as an organic acid in an organic solvent:

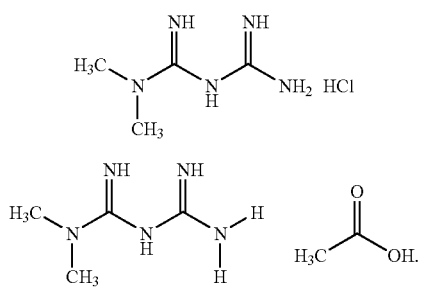

[Formula 4]

[Formula 1]

2. A method of preparing the metformin acetate of formula 1 in water as a solvent, which comprises reacting the metformin hydrochloride of formula 4 with acetic acid and inorganic base in an organic solvent in one reactor without special purifying process:

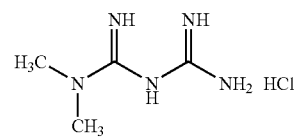

[Formula 4]

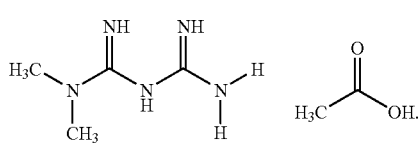

[Formula 1]

3. The method of preparing the metformin acetate of formula 1 according to claim 1 or 2, wherein the inorganic base is sodium hydroxide or potassium hydroxide.

4. The method of preparing the metformin acetate of formula 1 according to claim 1 or 2, wherein the molecular ratio of inorganic base reacting with 1 mole of the metformin hydrochloride is 1 to 2.

5. The method of preparing the metformin acetate of the formula 1 according to claim 1, wherein the molecular ratio of acetic acid reacting with 1 mole of the metformin free base is 1 to 2.

6. A method of preparing the metformin acetate of formula 1, which comprises reacting the metformin hydrochloride of formula 4 with organic alkali in water, and then reacting the resultant with acetic acid as an organic acid without removing inorganic salt:

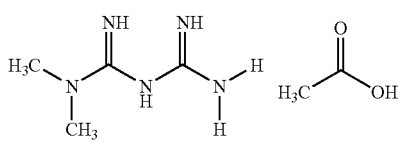

[Formula 1]

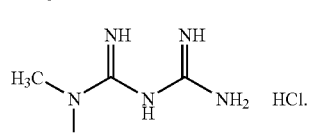

[Formula 4]

7. The method of preparing the metformin acetate of formula 1 according to claim 6, wherein the organic alkali is sodium hydrogen carbonate, potassium carbonate, sodium acetate or sodium acetate trihydrate.

8. The method of preparing the metformin acetate of formula 1 according to claim 6, wherein the molecular ratio of organic alkali reacting with 1 mole of the metformin hydrochloride is 1 to 2.

9. The method of preparing the metformin acetate of formula 1 according to any one of claims 1, 2 and 6, wherein the reaction is carried out in the temperature range of −10 to 50° C.

10. The method of preparing the metformin acetate of formula 1 according to claim 1 or 2, wherein the organic solvent is selected from the group consisting of water, methanol, ethanol, isopropanol, acetone and acetonitrile.

11. A method of treating diabetes mellitus or its complication, which comprises administrating to a patient a effective amount of a pharmaceutical composition containing the metformin acetate of formula 1 as an active ingredient:

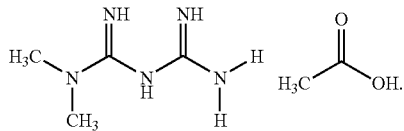

[Formula 1]

12. The method of claim 11, wherein the patient has metabolic syndromes.

13. The method of claim 11, wherein the diabetes mellitus is type 2 diabetes mellitus.

14. The method of claim 11, wherein the metformin acetate is orally administrated in amount of 50 to 3,000 mg per day.

15. The method of claim 11, wherein the metformin acetate is anhydrous metformin acetate.

16. A method of treating glycosuria, hypertension, hyperlipidemia, fatty liver, or coronary heart diseases, which comprises administrating to a patient a effective amount of a pharmaceutical composition containing the metformin acetate of formula 1 as an active ingredient:

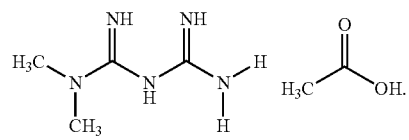

[Formula 1]

17. The method of claim 16, wherein the metformin acetate is anhydrous metformin acetate.

* * * * *